(12) United States Patent
Parikh et al.

(10) Patent No.: US 9,468,605 B2
(45) Date of Patent: Oct. 18, 2016

(54) FORMULATIONS OF (+)-2-[1-(3-ETHOXY-4-METHOXYPHENYL)-2-METHYLSULFONYLETHYL]-4-ACETYLAMINOISOINDOLINE-1,3-DIONE

(71) Applicant: Celgene Corporation, Summit, NJ (US)

(72) Inventors: Darshan K. Parikh, Bridgewater, NJ (US); Anil Menon, Martinsville, NJ (US); Anthony Tutino, New Providence, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/305,082

(22) Filed: Jun. 16, 2014

(65) Prior Publication Data

US 2014/0370092 A1     Dec. 18, 2014

Related U.S. Application Data

(60) Provisional application No. 61/840,210, filed on Jun. 27, 2013, provisional application No. 61/835,667, filed on Jun. 17, 2013.

(51) Int. Cl.
| | |
|---|---|
| A61K 9/28 | (2006.01) |
| A61K 31/4035 | (2006.01) |
| A61K 9/20 | (2006.01) |
| A61K 9/50 | (2006.01) |

(52) U.S. Cl.
CPC ........... *A61K 9/2866* (2013.01); *A61K 9/2018* (2013.01); *A61K 9/2077* (2013.01); *A61K 9/2846* (2013.01); *A61K 9/5084* (2013.01); *A61K 31/4035* (2013.01)

(58) Field of Classification Search
CPC ....................................................... A61K 9/20
See application file for complete search history.

(56) References Cited

U.S. PATENT DOCUMENTS

| | | | | |
|---|---|---|---|---|
| 4,964,848 | A * | 10/1990 | Bloom | .......................... 604/6.03 |
| 6,011,050 | A | 1/2000 | Muller et al. | |
| 6,020,358 | A | 2/2000 | Muller et al. | |
| 6,962,940 | B2 * | 11/2005 | Muller | ............... A61K 31/4035 514/417 |
| 7,208,526 | B2 | 4/2007 | Boyd et al. | |
| 7,659,302 | B2 | 2/2010 | Muller et al. | |
| 8,242,310 | B2 | 8/2012 | Saindane et al. | |
| 2008/0234359 | A1 | 9/2008 | Muller et al. | |
| 2010/0168475 | A1 | 7/2010 | Saindane et al. | |
| 2010/0324108 | A1 | 12/2010 | Liu | |
| 2011/0087033 | A1 | 4/2011 | Frank et al. | |
| 2013/0217918 | A1 | 8/2013 | Venkateswaralu et al. | |

FOREIGN PATENT DOCUMENTS

| | | | |
|---|---|---|---|
| DE | 2051871 | 11/1971 | |
| DE | WO 2012013567 A1 * | 2/2012 | ......... A61K 31/4035 |
| WO | WO 03/080048 A1 | 10/2003 | |
| WO | WO 2010/030345 | 3/2010 | |
| WO | WO 2012/083017 A2 | 6/2011 | |
| WO | WO 2012/097116 | 7/2012 | |
| WO | WO 2012/121988 A2 | 9/2012 | |

OTHER PUBLICATIONS

Lowe, 1998 "Tumour necrosis factor- antagonists and their therapeutic applications," Exp Opin Ther Patents 8(10):1309-1322.
McCann et al., 2010, "Apremilast, a novel PDE4 inhibitor, inhibits spontaneous production of tumour necrosis factor-alpha from human rheumatoid synovial cells and ameliorates experimental arthritis," Arthritis Res Ther; 12(3):R107.
Schett et al., 2010, "Apremilast: a novel PDE4 inhibitor in the treatment of autoimmune and inflammatory diseases", Ther Adv Musculoskel Dis; 2(5):271-278.
Lai C. et al., 2005, "One-pot approach for the regioselective synthesis of beta-keto sulfones based on acid-catalyzed reaction of sulfonyl chlorides with arylacetylenes and water", Tetrahedron Letters, Jan. 17, 2005, pp. 513-515, vol. 46, No. 3, Elsevier, Amsterdam, NL.
Velasquez et al., 2006, "Steroselective synthesis of beta-substituted beta-amino sulfones and sulfonamides via addition of sulfonyl anions to chiral N-sulfinyl imines," Organics Letters, vol. 8, No. 6, 2006, pp. 789-792.
Hua Zhang et al., 2011, "Practical and stereoselective synthesis of beta-amino sulfones from alkylphenylsulfones and N-(tert-butylsulfinyl)aldimines," Organic and Biomolecular Chemistry, vol. 9, 2011, pp. 6502-6505.
Guangcheng Liu et al., 1999, "Synthesis of enantiomerically pure N-tert-butanesulfinyl lmlnes (tert-butanesulfinimines) by the direct condensation of tert-butanesulfinamide with aldehydes and ketones," Journal of Organic Chemistry, vol. 64, No. 4, 1999, pp. 1278-1284.
Panteleimonov, A. G. et al., 1966, "Addition of nucleophilic agents to 1-aryl-2-trifluoro-methylsulfonylethylenes," Zhurnal Obshchei Khimii, 36(11), 1966, 1976-80, XP-002712273.
Balasubramanian M et al., 1955, "Synthesis of Beta-Amino-Sulphones and Alphabeta-Unsaturated Sulphones. Part 11," Journal of the Chemical Society, Chemical Society, Letchworth; GB, 1955, pp. 3296-3298, XP-001069585.
Baughman et al., 1990, "Release of tumor necrosis factor by alveolar macrophages of patients with sarcoidosis," *J. Lab. Clin. Med.* 115(1):36-42.
Beavo et al., 1990, "Primary sequence of cyclic nucleotide phosphodiesterase isozymes and the design of selective inhibitors," Trends in Pharmacol Sci, 11, 150-155, 1990.
Bissonnette et al., 1989, "Pulmonary inflammation and fibrosis in a murine model of asbestosis and silicosis. Possible role of tumor necrosis factor," *Inflammation* 13(3):329-339.

(Continued)

*Primary Examiner* — Frederick Krass
*Assistant Examiner* — Amanda Heyes
(74) *Attorney, Agent, or Firm* — Jones Day

(57) ABSTRACT

Pharmaceutical compositions and single unit dosage forms of apremilast, i.e., (+)-2-[1-(3-ethoxy-4-methoxyphenyl)-2-methylsulfonylethyl]-4-acetylaminoisoindoline-1,3-dione, or a pharmaceutically acceptable stereoisomer, prodrug, salt, solvate, hydrate, or clathrate, are provided herein. Also provided are methods of treating, managing, or preventing various disorders, such as diseases or disorders ameliorated by the inhibition of TNF-α production in mammals.

3 Claims, 8 Drawing Sheets

(56) References Cited

OTHER PUBLICATIONS

Clouse et al., 1989, "Monokine regulation of human immunodeficiency virus-1 expression in a chronically infected human T cell clone," *J. Immunol.* 142, 431-438.

Duh et al., 1989, "Tumor necrosis factor alpha activates human immunodeficiency virus type 1 through induction of nuclear factor binding to the NF-kappa B sites in the long terminal repeat," *Proc. Nat. Acad. Sci.* 86:5974-5978.

Folks et al., 1989, "Tumor necrosis factor alpha induces expression of human immunodeficiency virus in a chronically infected T-cell clone," PNAS 86(7):2365-2368.

Hinshaw et al., 1990, "Survival of primates in LD100 septic shock following therapy with antibody to tumor necrosis factor (TNF alpha)", Circ Shock, 30(3):279-92.

Holler et al., 1990, "Increased serum levels of tumor necrosis factor alpha precede major complications of bone marrow transplantation," Blood, 75(4):1011-6.

Johnson et al., 1989, "Tumors producing human tumor necrosis factor induced hypercalcemia and osteoclastic bone resorption in nude mice," Endocrinology, 124(3):1424-7.

Lowe et al., 1992, "Site-specific mutations in the COOH-terminus of placental alkaline phosphatase: a single amino acid change converts a phosphatidylinositol-glycan-anchored protein to a secreted protein." Drugs of the Future, J Cell Biol., 116(3):799-807.

Monte et al., 1990, "Productive human immunodeficiency virus-1 infection of megakaryocytic cells is enhanced by tumor necrosis factor-alpha," *Blood* 79(10):2670-9.

Poli et al., 1990, "Tumor necrosis factor alpha functions in an autocrine manner in the induction of human immunodeficiency virus expression," *Proc. Nat. Acad. Sci.* 87(2):782-785.

Poli et al., 1992, "The effect of cytokines and pharmacologic agents on chronic HIV infection," *AIDS Res. Hum. Retrovirus*, 8(2):191-197.

van Dullemen et al., 1995, "Treatment of Crohn's disease with anti-tumor necrosis factor chimeric monoclonal antibody (cA2)," *Gastroenterology*, 109:129-135.

Verghese, et al., 1995, "Differential regulation of human monocyte-derived TNF alpha and IL-1 beta by type IV cAMP-phosphodiesterase (cAMP-PDE) inhibitors," J Pharmacol Exp Ther, 272(3):1313-1320.

* cited by examiner

FORMULATIONS OF (+)-2-[1-(3-ETHOXY-4-METHOXYPHENYL)-2-METHYLSULFONYLETHYL]-4-ACETYLAMINOISOINDOLINE-1,3-DIONE

This application claims the benefit of U.S. Provisional Application No. 61/840,210, filed Jun. 27, 2013 and U.S. Provisional Application No. 61/835,667, filed Jun. 17, 2013, the entire contents of which are incorporated herein by reference.

FIELD

Provided herein are formulations and dosage forms of apremilast, i.e., (+)-2-[1-(3-ethoxy-4-methoxyphenyl)-2-methylsulfonylethyl]-4-acetylaminoisoindoline-1,3-dione. Methods of using the formulations and dosage forms are also provided herein.

BACKGROUND

Tumor necrosis factor alpha, (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood born tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

It is believed that the primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150-155, 1990). There are eleven known PDE families. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics*, 272(3), 1313-1320, 1995). Thus, compounds that inhibit PDE4 (PDE IV) specifically, may inhibit inflammation and aid the relaxation of airway smooth muscle with a minimum of unwanted side effects, such as cardiovascular or anti-platelet effects. Currently used PDE4 inhibitors lack the selective action at acceptable therapeutic doses.

Cancer is a particularly devastating disease, and increases in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. But increased levels of cytokines have been shown to substantially increase the adhesion of cancer cells to endothelium in vitro. One explanation is that cytokines, such as TNF-α, stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response, ELAM-1 on endothelial cells functions as a "homing receptor" for leukocytes. Recently, ELAM-1 on endothelial cells was shown to mediate the increased adhesion of colon cancer cells to endothelium treated with cytokines (Rice et al., 1989, *Science* 246:1303-1306).

Inflammatory diseases such as arthritis, related arthritic conditions (e.g., osteoarthritis and rheumatoid arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. TNF-α plays a central role in the inflammatory response and the administration of their antagonists block chronic and acute responses in animal models of inflammatory disease.

Enhanced or unregulated TNF-α production has been implicated in viral, genetic, inflammatory, allergic, and autoimmune diseases. Examples of such diseases include but are not limited to: HIV; hepatitis; adult respiratory distress syndrome; bone-resorption diseases; chronic obstructive pulmonary diseases; chronic pulmonary inflammatory diseases; asthma, dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; autoimmune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; ENL in leprosy; radiation damage; asthma; and hyperoxic alveolar injury. Tracey et al., 1987, *Nature* 330:662-664 and Hinshaw et al., 1990, *Circ. Shock* 30:279-292 (endotoxic shock); Dezube et al., 1990, *Lancet*, 335:662 (cachexia); Millar et al., 1989, *Lancet* 2:712-714 and Ferrai-Baliviera et al., 1989, *Arch. Surg.* 124:1400-1405 (adult respiratory distress syndrome); Bertolini et al., 1986, *Nature* 319:516-518, Johnson et al., 1989, *Endocrinology* 124:1424-1427, Holler et al., 1990, *Blood* 75:1011-1016, and Grau et al., 1989, *N. Engl. J. Med.* 320:1586-1591 (bone resorption diseases); Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109:129-135 (Crohn's disease); Duh et al., 1989, *Proc. Nat. Acad. Sci.* 86:5974-5978, Poll et al., 1990, *Proc. Nat. Acad. Sci.* 87:782-785, Monto et al., 1990, *Blood* 79:2670, Clouse et al., 1989, *J. Immunol.* 142, 431-438, Poll et al., 1992, *AIDS Res. Hum. Retrovirus*, 191-197, Poli et al. 1990, *Proc. Natl. Acad. Sci.* 87:782-784, Folks et al., 1989, *PNAS* 86:2365-2368 (HIV and opportunistic infections resulting from HIV).

Pharmaceutical compounds that can block the activity or inhibit the production of certain cytokines, including TNF-α, may be beneficial therapeutics. Many small-molecule inhibitors have demonstrated an ability to treat or prevent inflammatory diseases implicated by TNF-α (for a review, see Lowe, 1998 *Exp. Opin. Ther. Patents* 8:1309-1332). One such class of molecules are the substituted phenethylsulfones described in U.S. Pat. No. 6,020,358.

Due to its diversified pharmacological properties, apremilast is useful in treating, preventing, and/or managing various diseases or disorders. Thus, a need exists as to dosage forms of apremilast having advantageous physical and pharmaceutical properties, such as those suitable for once per day dosing.

SUMMARY

Provided herein are pharmaceutical dosage forms comprising the (+) enantiomer of 2-[1-(3-ethoxy-4-methoxyphenyl)-2-methylsulfonylethyl]-4-acetylaminoisoindoline-1,3-dione (apremilast), or a pharmaceutically acceptable stereoisomer, polymorph, prodrug, salt, hydrate, clathrate, or solvate thereof.

Without being limited by theory, it is thought that the compositions and dosage forms provided herein are suitable for once daily dosing of ampremilast and also result in reduced gastrointestinal adverse effects relative to dosing regimens comprising more than one dose per day.

Further provided herein are methods for using the compositions and pharmaceutical dosage forms of the (+) enantiomer of 2-[1-(3-ethoxy-4-methoxyphenyl)-2-methylsulfonylethyl]-4-acetylaminoisoindoline-1,3-dione for treating, managing or preventing diseases or disorders ameliorated by the inhibition of TNF-α production in mammals. In certain embodiments, this treatment includes the reduction or avoidance of adverse effects. Such diseases or disorders include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated include multiple myeloma, malignant melanoma, malignant glioma, leukemia and solid tumors.

Further provided herein are methods for using the compositions and pharmaceutical dosage forms of the (+) enantiomer of 2-[1-(3-ethoxy-4-methoxyphenyl)-2-methylsulfonylethyl]-4-acetylaminoisoindoline-1,3-dione in the treatment or prevention of heart disease, including, but not limited to congestive heart failure, cardiomyopathy, pulmonary edema, endotoxin-mediated septic shock, acute viral myocarditis, cardiac allograft rejection, and myocardial infarction.

Further provided herein are methods for using the compositions and pharmaceutical dosage forms of the (+) enantiomer of 2-[1-(3-ethoxy-4-methoxyphenyl)-2-methylsulfonylethyl]-4-acetylaminoisoindoline-1,3-dione to treat diseases or disorders ameliorated by the inhibition of PDE4. For example, the compositions and pharmaceutical dosage forms provided herein may be useful to treat or prevent viral, genetic, inflammatory, allergic, and autoimmune diseases. Examples of such diseases include, but are not limited to: HIV; hepatitis; adult respiratory distress syndrome; bone-resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic reperfusion injury; meningitis; psoriasis; fibrotic disease; cachexia; graft rejection including graft versus host disease; auto-immune disease; rheumatoid spondylitis; arthritic conditions, such as psoriatic arthritis, rheumatoid arthritis and osteoarthritis; osteoporosis; Crohn's disease; ulcerative colitis; inflammatory-bowel disease; multiple sclerosis; systemic lupus erythrematosus; erythema nodosum leprosum (ENL) in leprosy; radiation damage; asthma; and hyperoxic alveolar injury.

In yet another embodiment, the compositions and pharmaceutical dosage forms of the (+) enantiomer of 2-[1-(3-ethoxy-4-methoxyphenyl)-2-methylsulfonylethyl]-4-acetylaminoisoindoline-1,3-dione are also useful in the treatment or prevention of microbial infections or the symptoms of microbial infections including, but not limited to, bacterial infections, fungal infections, malaria, mycobacterial infection, and opportunistic infections resulting from HIV.

Definitions

Figure 1:
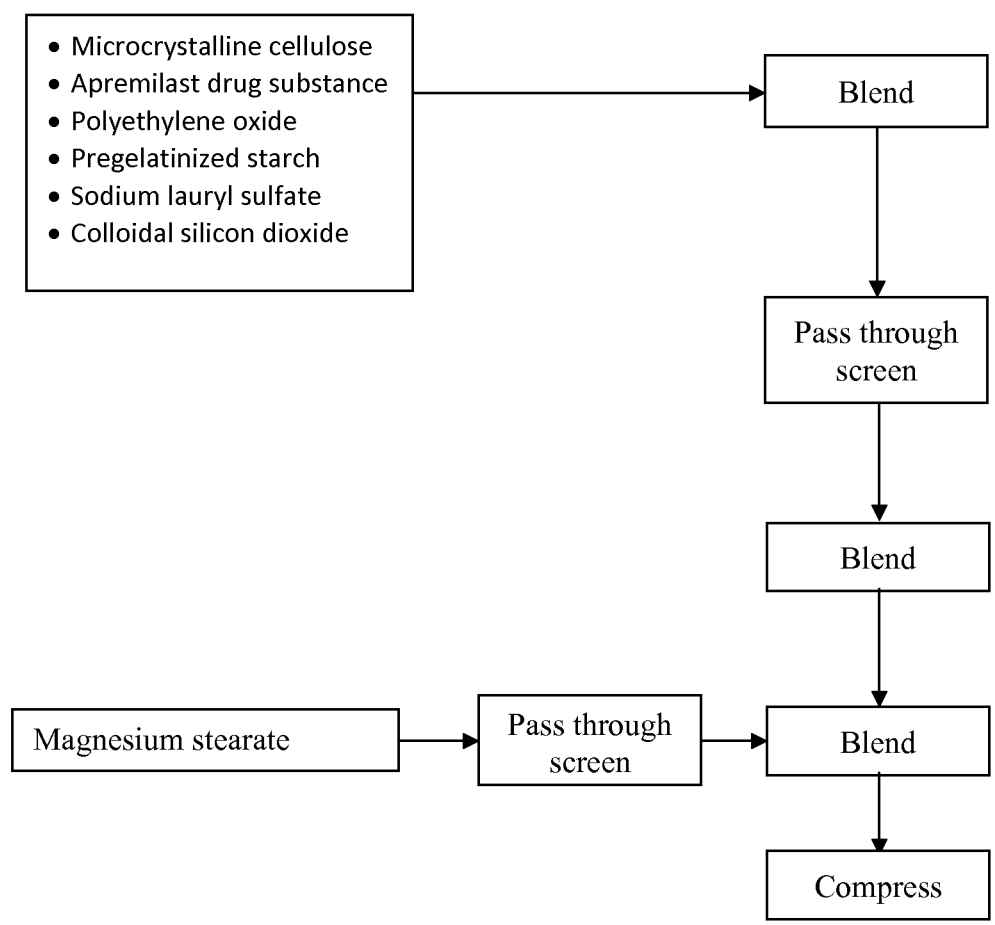
FIG. 1: Process flow diagram for the manufacture of apremilast modified released (MR) tablet.

As used herein, term "apremilast" refers to an enantiomerically pure form of 2-[1-(3-ethoxy-4-methoxyphenyl)-2-methylsulfonylethyl]-4-acetylaminoisoindoline-1,3-dione. In one embodiment, the apremilast is what comes off of an HPLC column at about 25.4 minutes when that column is a 150 mm×4.6 mm Ultron Chiral ES-OVS chiral HPLC column (Agilent Technology), the eluent is 15:85 ethanol: 20 mM $KH_2PO_4$ at pH 3.5, and the observation wavelength is 240 nm. The $^1H$ NMR spectrum of apremilast is substantially as follows: δ($CDCl_3$): 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). The $^{13}C$ NMR spectrum of apremilast is substantially as follows δ(DMSO-$d_6$): 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48. Apremilast dissolved in methanol also rotates plane polarized light in the (+) direction.

Without being limited by theory, apremilast is believed to be S-{2-[1-(3-ethoxy-4-methoxyphenyl)-2-methylsulfonylethyl]-4-acetylaminoisoindoline-1,3-dione}, which has the following structure:

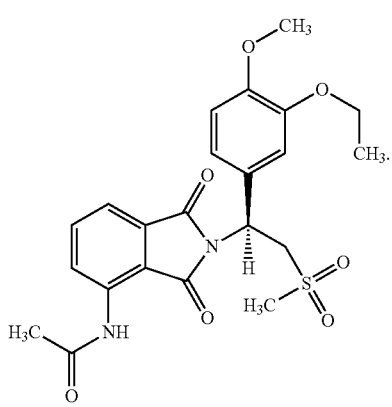

As used herein, the term "pharmaceutically acceptable salts" refer to salts prepared from pharmaceutically acceptable non-toxic acids or bases including inorganic acids and bases and organic acids and bases.

As used herein, term "Compound A" refers to apremilast, or a pharmaceutically acceptable salt, stereoisomer, prodrug, solvate, hydrate, clathrate, isotopologue, metabolite or solid form thereof.

As used herein, the term "patient" refers to a mammal, particularly a human.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, even more preferably greater than about 97 percent by weight of one stereoisomer of the compound and less than about 3 percent by weight of the other stereoisomers of the compound, and most preferably greater than about 99 percent by weight of one stereoisomer of the compound and less than about 1 percent by weight of the other stereoisomers of the compound.

As used herein and unless otherwise indicated, the term "enantiomerically pure" means a stereomerically pure composition of a compound having one chiral center.

As used herein, unless otherwise specified, the term "pharmaceutically acceptable salt(s)," as used herein includes, but is not limited to, salts of acidic or basic moieties of apremilast. Basic moieties are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of apremilast that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of apremilast that include —NO, —NO$_2$, —ONO, or —ONO$_2$ moieties.

As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, and unless otherwise specified, the terms "treat," "treating" and "treatment" contemplate an action that occurs while a patient is suffering from the specified disease or disorder, which reduces the severity of the disease or disorder, or retards or slows the progression of the disease or disorder.

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, and unless otherwise specified, the term "stable," when used in connection with a formulation or a dosage form, means that the active ingredient of the formulation or dosage form remains solubilized for a specified amount of time and does not significantly degrade or aggregate or become otherwise modified (e.g., as determined, for example, by HPLC). In some embodiments, about 70 percent or greater, about 80 percent or greater or about 90 percent or greater of the compound remains solubilized after the specified period.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

The phrases "therapeutically effective amount", "prophylactically effective amount" and "therapeutically or prophylactically effective amount," as used herein encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause, or sufficient to reduce, adverse effects associated with racemic 2-[1-(3-ethoxy-4-methoxyphenyl)-2-methylsulfonylethyl]-4-acetylaminoisoindoline-1,3-dione are also encompassed by the above described dosage amounts and dose frequency schedules.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

DETAILED DESCRIPTION

Provided herein are pharmaceutical compositions and dosage forms of Compound A. In some embodiments, the dosage forms are suitable for oral administration to a patient. In other embodiments, the dosage forms provided herein exhibit advantageous physical and/or pharmacological properties. Such properties include, but are not limited to, ease of assay, content uniformity, flow properties for manufacture, dissolution and bioavailability, and stability. In certain embodiments, the dosage forms provided herein have a shelf life of at least about 12 months, at least about 24 months, or at least about 36 months without refrigeration.

In certain embodiments, the pharmaceutical compositions and dosage forms provided herein are designed to release Compound A throughout the gastrointestinal tract. In certain embodiments, the compositions and dosage forms are designed to allow for pH-dependent release of Compound A in the gastrointestinal tract. In certain embodiments, the compositions and dosage forms are designed to allow for pH-independent release of Compound A in the gastrointestinal tract.

In certain embodiments, the pharmaceutical compositions and dosage forms provided herein are tailored to provide once a day dosing option in order to enhance patient compliance and to reduce or eliminate peaks and troughs associated with twice a day dosing.

Also provided herein are kits comprising pharmaceutical compositions and dosage forms provided herein. Also provided herein are methods of treating, managing, and/or preventing a disease or condition, which comprises administering to a patient in need thereof a pharmaceutical composition or a dosage form provided herein.

In certain embodiments, the pharmaceutical compositions and dosage forms provided herein are capsule dosage forms. In certain embodiments, the pharmaceutical compositions and dosage forms provided herein are tablets.

In certain embodiments, the pharmaceutical compositions and dosage forms provided herein are multiparticulate formulations. In certain embodiments, the multiparticulate formulations comprise discrete units. In certain embodiments, the multiparticulates are minitabs or minitablets.

In one embodiment, the dosage form is suitable for administration in a size 4 or larger capsule.

6.1 Compositions and Dosage Forms 6.1.1 Formulation A

In one embodiment, provided herein is a pharmaceutical composition comprising Compound A, and one or more pharmaceutically acceptable excipients or carriers.

In one embodiment, provided herein is a pharmaceutical composition comprising Compound A and one or more pharmaceutically acceptable excipients and carriers selected from diluents, surfactants, disintegrants, glidants and lubricants. In certain embodiments, the pharmaceutical compositions can be coated.

In certain embodiments, the diluents include, but are not limited to, lactose (e.g., lactose monohydrate (FAST FLO® 316)), cellulose (e.g., microcrystalline cellulose, such as AVICEL® PH 101 and AVICEL® PH 102). In one embodiment, the diluent is lactose. In another embodiment, the diluent is lactose monohydrate. In yet another embodiment, the diluent is FAST FLO® 316. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, organosulfate (e.g., sodium lauryl sulfate). In one embodiment, the surfactant is sodium lauryl sulfate.

In certain embodiments, the disintegrants include, but are not limited to, carboxymethyl cellulose (e.g., croscarmellose sodium, such as AC-DI-SOL®). In one embodiment, the disintegrant is carboxymethyl cellulose. In another embodiment, the disintegrant is croscarmellose sodium. In still another embodiment, the disintegrant is AC-DI-SOL®.

In certain embodiments, the glidants include, but are not limited to fumed silica (e.g., silicon oxide, such as colloidal silicon dioxide). In one embodiment, the gilant is fumed silica. In another embodiment, the gilant is silicon oxide. In another embodiment, the gilant is colloidal silicon dioxide.

In certain embodiments, the lubricants include, but are not limited to, magnesium stearate (e.g., magnesium stearate, vegetable source). In one embodiment, the lubricant is magnesium stearate. In another embodiment, the lubricant is magnesium stearate, vegetable source.

In certain embodiments, the coats include, but are not limited to, Opadry (e.g., Opadry clear). In one embodiment, the coat is Opadry. In another embodiment, the coat is Opadry clear.

In certain embodiments, provided herein are pharmaceutical compositions comprising Compound A and one or more pharmaceutically acceptable excipients or carriers, each independently selected from lactose, cellulose, organosulfate, carboxymethyl cellulose, fumed silica and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from lactose monohydrate, microcrystalline cellolose, sodium lauryl sulfate, croscarmellose sodium, silicon dioxide and magnesium stearate. In certain embodiments, the pharmaceutical compositions are coated with Opadry.

In certain embodiments, provided herein are pharmaceutical compositions comprising Compound A and one or more pharmaceutically acceptable excipients or carriers, each independently selected from FAST FLO® 316, AVICEL® PH 101, sodium lauryl sulfate, AC-DI-SOL®, colloidal silicon dioxide and magnesium stearate vegetable source. In certain embodiments, the pharmaceutical compositions are coated with Opadry clear.

In one embodiment, provided herein is a pharmaceutical composition comprising Compound A, a diluent(s)/binder(s), a surfactant(s), a disintegratnt(s), a glidant(s) and a lubricant(s). In certain embodiments, the pharmaceutical compositions can be coated. In certain embodiments, the pharmaceutical compositions can be modifed-release-coated.

In one embodiment, provided herein is a pharmaceutical composition comprising Compound A, lactose and magnesium stearate.

In one embodiment, provided herein is a pharmaceutical composition comprising Compound A, lactose, cellulose and magnesium stearate.

In certain embodiments, provided herein are pharmaceutical compositions comprising Compound A, lactose monohydrate, microcrystalline cellulose, organosulfate, carboxymethyl cellulose, fumed silica and magnesium stearate.

In certain embodiments, provided herein are pharmaceutical compositions comprising Compound A, lactose monohydrate, microcrystalline cellulose, organosulfate, croscarmellose sodium, colloidal silicon dioxide and magnesium stearate.

In certain embodiments, provided herein are pharmaceutical compositions comprising Compound A, FAST FLO 316®, AVICEL PH 102®, AC-DI-SOL®, and magnesium stearate.

In one embodiment, provided herein is a pharmaceutical composition comprising about 10-30% by weight of Compound A, about 60-80% by weight of diluent(s)/binder(s), about 1-5% by weight of surfactant(s), about 1-5% by weight of disintegrant(s), about 1-5% by weight of glidant(s), about 0.1-2% by weight of lubricant(s) and about 1-5% by weight of coat(s).

In one embodiment, provided herein is a pharmaceutical composition comprising about 19.23% by weight of Compound A, about 68.47% by weight of diluent(s)/binder(s), about 2.90% by weight of surfactant(s), about 2.90% by weight of disintegrant(s), about 1.95% by weight of glidant(s), about 0.72% by weight of lubricant(s) and about 3.85% by weight of coat(s).

In one embodiment, provided herein is a pharmaceutical composition comprising about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry.

In one embodiment, provided herein is a pharmaceutical composition comprising about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry.

In one embodiment, provided herein is a pharmaceutical composition comprising about 19% by weight of Compound A, about 43% by weight of lactose, about 25% by weight of cellulose, about 3% by weight of organosulfate, about 3% by weight of carboxymethyl cellulose, about 2% by weight of fumed silica, about 1% by weight of magnesium stearate and about 4% by weight of Opadry.

In one embodiment, provided herein is a pharmaceutical composition comprising about 19.23% by weight of Compound A, about 43.44% by weight of lactose, about 25.03% by weight of cellulose, about 2.90% by weight of organosulfate, about 2.90% by weight of carboxymethyl cellulose, about 1.95% by weight of fumed silica, about 0.72% by weight of magnesium stearate and about 3.85% by weight of Opadry.

In one embodiment, provided herein is a pharmaceutical composition comprising about 10-30% by weight of Compound A, about 40-50% by weight of lactose monohydrate, about 20-30% by weight of microcrystalline cellulose, about 1-5% by weight of sodium lauryl sulfate, about 1-5% by weight of croscarmellose sodium, about 1-5% by weight of colloidal silicon dioxide, about 0.1-2% by weight of magnesium stearate and about 1-5% by weight of Opadry.

In one embodiment, provided herein is a pharmaceutical composition comprising about 19% by weight of Compound A, about 43% by weight of lactose monohydrate, about 25% by weight of microcrystalline cellulose, about 3% by weight of sodium lauryl sulfate, about 3% by weight of croscarmellose sodium, about 2% by weight of colloidal silicon dioxide, about 1% by weight of magnesium stearate and about 4% by weight of Opadry.

In one embodiment, provided herein is a pharmaceutical composition comprising about 19.23% by weight of Compound A, about 43.44% by weight of lactose monohydrate, about 25.03% by weight of microcrystalline cellulose, about 2.90% by weight of sodium lauryl sulfate, about 2.90% by weight of croscarmellose sodium, about 1.95% by weight of colloidal silicon dioxide, about 0.72% by weight of magnesium stearate and about 3.85% by weight of Opadry.

In one embodiment, provided herein is a pharmaceutical composition comprising about 10-30% by weight of Compound A, about 40-50% by weight of FAST FLO® 316, about 20-30% by weight of AVICEL® PH 101 or AVICEL® PH 102, about 1-5% by weight of sodium lauryl sulfate, about 1-5% by weight of AC DI SOLO, about 1-5% by weight of colloidal silicon dioxide, about 0.1-2% by weight of magnesium stearate vegetable source and about 1-5% by weight of Opadry clear.

In one embodiment, provided herein is a pharmaceutical composition comprising about 19.23% by weight of Compound A, about 43.44% by weight of FAST FLO® 316, about 25.03% by weight of AVICEL® PH 101 or AVICEL® PH 102, about 2.90% by weight of sodium lauryl sulfate, about 2.90% by weight of AC-DI-SOL®, about 1.95% by weight of colloidal silicon dioxide, about 0.72% by weight of magnesium stearate vegetable source and about 3.85% by weight of Opadry clear.

In certain embodiments, the weight of a pharmaceutical composition is about 5-15 mg. In one embodiment, the pharmaceutical composition comprises about 0.5-3 mg Compound A, about 2-10 mg diluent(s)/binder(s), about 0.1-1 mg surfactant(s), about 0.1-1 mg disintegrant(s), about 0.05-0.5 mg glidant(s), about 0.01-0.3 mg lubricant(s) and about 0.1-0.5 mg coat(s).

In certain embodiments, the weight of a pharmaceutical composition is about 7.8 mg. In one embodiment, the pharmaceutical composition comprises about 1.5 mg Compound A, about 5.34 mg diluent(s)/binder(s), about 0.226 mg surfactant(s), about 0.226 mg disintegrant(s), about 0.152 mg glidant(s), about 0.056 mg lubricant(s) and about 0.3 mg coat(s).

In certain embodiments, the weight of a pharmaceutical composition is about 5-15 mg and comprises about 0.5-3 mg Compound A, about 1-5 mg lactose, about 1-5 mg cellulose, about 0.1-1 mg organosulfate, about 0.1-1 mg carboxymethyl cellulose, about 0.05-0.5 mg fumed silica, about 0.01-0.3 mg magnesium stearate and about 0.1-0.5 mg Opadry.

In certain embodiments, the weight of a pharmaceutical composition is about 7.8 mg and comprises about 1.5 mg Compound A, about 3.388 mg lactose, about 1.952 mg cellulose, about 0.226 mg organosulfate, about 0.226 mg carboxymethyl cellulose, about 0.152 mg fumed silica, about 0.056 mg magnesium stearate and about 0.300 mg Opadry.

In certain embodiments, the weight of a pharmaceutical composition is about 5-15 mg and comprises about 0.5-3 mg Compound A, about 1-5 mg lactose monohydrate, about 1-5 mg microcrystalline cellulose, about 0.1-1 mg sodium lauryl sulfate, about 0.1-1 mg croscarmellose sodium, about 0.05-0.5 mg colloidal silicon dioxide, about 0.01-0.3 mg magnesium stearate and about 0.1-0.5 mg Opadry.

In certain embodiments, the weight of a pharmaceutical composition is about 7.8 mg and comprises about 1.5 mg Compound A, about 3.388 mg lactose monohydrate, about 1.952 mg microcrystalline cellulose, about 0.226 mg sodium lauryl sulfate, about 0.226 mg croscarmellose sodium, about 0.152 mg colloidal silicon dioxide, about 0.056 mg magnesium stearate and about 0.300 mg Opadry.

In certain embodiments, the weight of a pharmaceutical composition is about 5-15 mg and comprises about 0.5-3 mg Compound A, about 1-5 mg FAST FLO® 316, about 1-5 mg AVICEL® PH 101 or AVICEL® PH 102, about 0.1-1 mg sodium lauryl sulfate, about 0.1-1 mg AC DI SOL®, about 0.05-0.5 mg colloidal silicon dioxide, about 0.01-0.3 mg magnesium stearate vegetable source and about 0.1-0.5 mg Opadry clear.

In certain embodiments, the weight of a pharmaceutical composition is about 7.8 mg and comprises about 1.5 mg Compound A, about 3.388 mg FAST FLO® 316, about 1.952 mg AVICEL® PH 101 or AVICEL® PH 102, about 0.226 mg sodium lauryl sulfate, about 0.226 mg AC DI SOL®, about 0.152 mg colloidal silicon dioxide, about 0.056 mg magnesium stearate vegetable source and about 0.300 mg Opadry clear.

6.1.2 Formulation B

In one embodiment, provided herein is a pharmaceutical composition comprising Compound A and one or more pharmaceutically acceptable excipients and carriers selected from diluents, surfactants, disintegrants, glidants, lubricants, polymers and plasticizers. In certain embodiments, the pharmaceutical compositions can be modifed-release-coated.

In certain embodiments, the diluents include, but are not limited to, lactose (e.g., lactose monohydrate (FAST FLO® 316)), cellulose (e.g., microcrystalline cellulose, such as AVICEL® PH 101 and AVICEL® PH 102). In one embodiment, the diluent is lactose. In another embodiment, the diluent is lactose monohydrate. In yet another embodiment, the diluent is FAST FLO® 316. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102).

In certain embodiments, the surfactants include, but are not limited to, organosulfate (e.g., sodium lauryl sulfate). In one embodiment, the surfactant is sodium lauryl sulfate.

In certain embodiments, the disintegrants include, but are not limited to, carboxymethyl cellulose (e.g., croscarmellose sodium, such as AC-DI-SOL®). In one embodiment, the disintegrant is carboxymethyl cellulose. In another embodiment, the disintegrant is croscarmellose sodium. In still another embodiment, the disintegrant is AC-DI-SOL®.

In certain embodiments, the glidants include, but are not limited to fumed silica (e.g., silicon oxide, such as colloidal silicon dioxide). In one embodiment, the gilant is silicon oxide. In another embodiment, the gilant is colloidal silicon dioxide.

In certain embodiments, the lubricants include, but are not limited to, magnesium stearate (e.g., magnesium stearate, vegetable source). In one embodiment, the lubricant is magnesium stearate. In another embodiment, the lubricant is magnesium stearate, vegetable source.

In certain embodiments, the polymers include, but are not limited to, poly(methacrylic acid, ethyl acrylate) (e.g., poly (methacrylic acid, ethyl acrylate) white). In one embodiment, the modified-release coat is poly(methacrylic acid, ethyl acrylate). In another embodiment, the modified-release coat is poly(methacrylic acid, ethyl acrylate) white. In another embodiment, the modified-release coat is poly (methacrylic acid, ethyl acrylate, 1:1) white.

In certain embodiments, the plasticizers include, but are not limited to, triethyl citrate. In one embodiment, the plasticizer is triethyl citrate.

In certain embodiments, the coats include, but are not limited to, Opadry (e.g., Opadry clear). In one embodiment, the coat is Opadry. In another embodiment, the coat is Opadry clear.

In certain embodiments, provided herein are pharmaceutical compositions comprising Compound A and one or more pharmaceutically acceptable excipients or carriers, each independently selected from lactose, cellulose, organosulfate, carboxymethyl cellulose, fumed silica, magnesium stearate, poly(methacrylic acid, ethyl acrylate) and triethyl citrate. In certain embodiments, the pharmaceutical compositions are coated with Opadry. In certain embodiments, the pharmaceutical compositions are modifed-release-coated with poly(methacrylic acid, ethyl acrylate).

In certain embodiments, provided herein are pharmaceutical compositions comprising Compound A and one or more pharmaceutically acceptable excipients or carriers, each independently selected from lactose monohydrate, microcrystalline cellolose, sodium lauryl sulfate, croscarmellose sodium, silicon dioxide, magnesium stearate, poly(methacrylic acid, ethyl acrylate) and triethyl citrate. In certain embodiments, the pharmaceutical compositions are coated with Opadry. In certain embodiments, the pharmaceutical compositions are modifed-release-coated with poly(methacrylic acid, ethyl acrylate).

In certain embodiments, provided herein are pharmaceutical compositions comprising Compound A and one or more pharmaceutically acceptable excipients or carriers, each independently selected from FAST FLO® 316, AVICEL® PH 101, sodium lauryl sulfate, AC-DI-SOL®, colloidal silicon dioxide, magnesium stearate vegetable source, poly (methacrylic acid, ethyl acrylate) white and triethyl citrate. In certain embodiments, the pharmaceutical compositions are coated with Opadry clear. In certain embodiments, the pharmaceutical compositions are modifed-release-coated with poly(methacrylic acid, ethyl acrylate) white.

In one embodiment, provided herein is a pharmaceutical composition comprising Compound A, a diluent(s)/binder (s), a surfactant(s), a disintegratnt(s), a glidant(s), a lubricant (s), a polymer(s), a plasticizer(s). In certain embodiments, the pharmaceutical compositions can be modifed-release-coated.

In one embodiment, provided herein is a pharmaceutical composition comprising Compound A, lactose and magnesium stearate.

In one embodiment, provided herein is a pharmaceutical composition comprising Compound A, lactose, cellulose and magnesium stearate.

In certain embodiments, provided herein are pharmaceutical compositions comprising Compound A, lactose monohydrate, microcrystalline cellulose, organosulfate, carboxymethyl cellulose, fumed silica and magnesium stearate.

In certain embodiments, provided herein are pharmaceutical compositions comprising Compound A, lactose monohydrate, microcrystalline cellulose, organosulfate, croscarmellose sodium, colloidal silicon dioxide, poly(methacrylic acid, ethyl acrylate), triethyl citrate, and magnesium stearate.

In certain embodiments, provided herein are pharmaceutical compositions comprising Compound A, FAST FLO 316®, AVICEL PH 102®, AC-DI-SOL®, poly(methacrylic acid, ethyl acrylate) white, triethyl citrate and magnesium stearate.

In one embodiment, provided herein is a pharmaceutical composition comprising about 5-30% by weight of Compound A, about 30-70% by weight of diluent(s)/binder(s), about 1-5% by weight of surfactant(s), about 1-5% by weight of disintegrant(s), about 0.5-5% by weight of glidant (s), about 0.1-2% by weight of lubricant(s), about 10-50% by weight of polymer(s), about 1-10% by weight of plasticizer(s) and about 1-10% by weight of coat(s) (including modified-release coat(s)).

In one embodiment, provided herein is a pharmaceutical composition comprising about 13.33% by weight of Compound A, about 47.47% by weight of diluent(s)/binder(s), about 2.01% by weight of surfactant(s), about 2.01% by weight of disintegrant(s), about 1.35% by weight of glidant (s), about 0.50% by weight of lubricant(s), about 25.21% by weight of polymer(s), about 2.52% by weight of plasticizer (s) and about 5.58% by weight of coat(s) (including modified-release coat(s)).

In one embodiment, provided herein is a pharmaceutical composition comprising about 5-30% by weight of Compound A, about 15-45% by weight of lactose, about 5-30% by weight of cellulose, about 1-5% by weight of organosulfate, about 1-5% by weight of carboxymethyl cellulose, about 0.5-5% by weight of fumed silica, about 0.1-2% by weight of magnesium stearate, about 10-50% by weight of poly(methacrylic acid, ethyl acrylate), about 1-10% by weight of triethyl citrate and about 1-10% by weight of Opadry.

In one embodiment, provided herein is a pharmaceutical composition comprising about 5-30% by weight of Compound A, about 15-45% by weight of lactose, about 5-30% by weight of cellulose, about 0-10% by weight of organosulfate, about 1-5% by weight of carboxymethyl cellulose, about 0.5-5% by weight of fumed silica, about 0.1-2% by weight of magnesium stearate, about 5-50% by weight of poly(methacrylic acid, ethyl acrylate), about 1-10% by weight of triethyl citrate and about 1-10% by weight of Opadry.

In one embodiment, provided herein is a pharmaceutical composition comprising about 13% by weight of Compound A, about 30% by weight of lactose, about 17% by weight of cellulose, about 2% by weight of organosulfate, about 2% by weight of carboxymethyl cellulose, about 1% by weight of fumed silica, about 1% by weight of magnesium stearate, about 25% by weight of poly(methacrylic acid, ethyl acrylate), about 3% by weight of triethyl citrate and about 6% by weight of Opadry.

In one embodiment, provided herein is a pharmaceutical composition comprising about 13.33% by weight of Compound A, about 30.12% by weight of lactose, about 17.35% by weight of cellulose, about 2.01% by weight of organosulfate, about 2.01% by weight of carboxymethyl cellulose, about 1.35% by weight of fumed silica, about 0.50% by weight of magnesium stearate, about 25.21% by weight of poly(methacrylic acid, ethyl acrylate), about 2.52% by weight of triethyl citrate and about 5.58% by weight of Opadry.

In one embodiment, provided herein is a pharmaceutical composition comprising about 5-30% by weight of Compound A, about 15-45% by weight of lactose monohydrate, about 5-30% by weight of microcrystalline cellulose, about 1-5% by weight of sodium lauryl sulfate, about 1-5% by weight of croscarmellose sodium, about 0.5-5% by weight of colloidal silicon dioxide, about 0.1-2% by weight of magnesium stearate, about 10-50% by weight of poly(methacrylic acid, ethyl acrylate), about 1-10% by weight of triethyl citrate and about 1-10% by weight of Opadry.

In one embodiment, provided herein is a pharmaceutical composition comprising about 13% by weight of Compound A, about 30% by weight of lactose monohydrate, about 17% by weight of microcrystalline cellulose, about 2% by weight of sodium lauryl sulfate, about 2% by weight of croscarmellose sodium, about 1% by weight of colloidal silicon dioxide, about 1% by weight of magnesium stearate, about 25% by weight of poly(methacrylic acid, ethyl acrylate), about 3% by weight of triethyl citrate and about 6% by weight of Opadry.

In one embodiment, provided herein is a pharmaceutical composition comprising about 13.33% by weight of Compound A, about 30.12% by weight of lactose monohydrate, about 17.35% by weight of microcrystalline cellulose, about 2.01% by weight of sodium lauryl sulfate, about 2.01% by weight of croscarmellose sodium, about 1.35% by weight of colloidal silicon dioxide, about 0.50% by weight of magnesium stearate, about 25.21% by weight of poly(methacrylic acid, ethyl acrylate), about 2.52% by weight of triethyl citrate and about 5.58% by weight of Opadry.

In one embodiment, provided herein is a pharmaceutical composition comprising about 5-30% by weight of Compound A, about 15-45% by weight of FAST FLO® 316, about 5-30% by weight of AVICEL® PH 101 or AVICEL® PH 102, about 1-5% by weight of sodium lauryl sulfate, about 1-5% by weight of AC DI SOLO, about 0.5-5% by weight of colloidal silicon dioxide, about 0.1-2% by weight of magnesium stearate vegetable source, about 10-50% by weight of poly(methacrylic acid, ethyl acrylate) white, about 1-10% by weight of triethyl citrate and about 1-10% by weight of Opadry clear.

In one embodiment, provided herein is a pharmaceutical composition comprising about 13.33% by weight of Compound A, about 30.12% by weight of FAST FLO® 316, about 17.35% by weight of AVICEL® PH 101 or AVICEL® PH 102, about 2.01% by weight of sodium lauryl sulfate, about 2.01% by weight of AC-DI-SOL®, about 1.35% by weight of colloidal silicon dioxide, about 0.50% by weight of magnesium stearate vegetable source, about 25.21% by weight of poly(methacrylic acid, ethyl acrylate) white, about 2.52% by weight of triethyl citrate and about 5.58% by weight of Opadry clear.

In certain embodiments, the weight of a pharmaceutical composition is about 5-20 mg. In one embodiment, the pharmaceutical composition comprises about 0.5-3 mg Compound A, about 2-10 mg diluent(s)/binder(s), about 0.1-1 mg surfactant(s), about 0.1-1 mg disintegrant(s), about 0.05-0.5 mg glidant(s), about 0.01-0.3 mg lubricant(s), about 1-5 mg polymer(s), about 0.1-1 mg plasticizer(s) and about 0.1-1 mg coat(s) (including modified-release coat(s)).

In certain embodiments, the weight of a pharmaceutical composition is about 11.248 mg. In one embodiment, the pharmaceutical composition comprises about 1.5 mg Compound A, about 5.34 mg diluent(s)/binder(s), about 0.226 mg surfactant(s), about 0.226 mg disintegrant(s), about 0.152 mg glidant(s), about 0.056 mg lubricant(s), about 2.836 mg polymer(s), about 0.284 mg plasticizer(s) and about 0.628 mg coat(s) (including modified-release coat(s)).

In certain embodiments, the weight of a pharmaceutical composition is about 5-20 mg and comprises about 0.5-3 mg Compound A, about 1-5 mg lactose, about 1-5 mg cellulose, about 0.1-1 mg organosulfate, about 0.1-1 mg carboxymethyl cellulose, about 0.05-0.5 mg fumed silica, about 0.01-0.3 mg magnesium stearate, about 1-5 mg poly(methacrylic acid, ethyl acrylate), about 0.1-1 mg triethyl citrate and about 0.1-1 mg Opadry.

In certain embodiments, the weight of a pharmaceutical composition is about 11.248 mg and comprises about 1.5 mg Compound A, about 3.388 mg lactose, about 1.952 mg cellulose, about 0.226 mg organosulfate, about 0.226 mg carboxymethyl cellulose, about 0.152 mg fumed silica, about 0.056 mg magnesium stearate, about 2.836 mg poly(methacrylic acid, ethyl acrylate), about 0.284 mg triethyl citrate and about 0.628 mg Opadry.

In certain embodiments, the weight of a pharmaceutical composition is about 5-20 mg and comprises about 0.5-3 mg Compound A, about 1-5 mg lactose monohydrate, about 1-5 mg microcrystalline cellulose, about 0.1-1 mg sodium lauryl sulfate, about 0.1-1 mg croscarmellose sodium, about 0.05-0.5 mg colloidal silicon dioxide, about 0.01-0.3 mg magnesium stearate, about 1-5 mg poly(methacrylic acid, ethyl acrylate), about 0.1-1 mg triethyl citrate and about 0.1-1 mg Opadry.

In certain embodiments, the weight of a pharmaceutical composition is about 11.248 mg and comprises about 1.5 mg Compound A, about 3.388 mg lactose monohydrate, about 1.952 mg microcrystalline cellulose, about 0.226 mg sodium lauryl sulfate, about 0.226 mg croscarmellose sodium, about 0.152 mg colloidal silicon dioxide, about 0.056 mg magnesium stearate, about 2.836 mg poly(methacrylic acid, ethyl acrylate), about 0.284 mg triethyl citrate and about 0.628 mg Opadry.

In certain embodiments, the weight of a pharmaceutical composition is about 5-20 mg and comprises about 0.5-3 mg Compound A, about 1-5 mg FAST FLOC) 316, about 1-5 mg AVICEL® PH 101 or AVICEL® PH 102, about 0.1-1 mg sodium lauryl sulfate, about 0.1-1 mg AC DI SOL®, about 0.05-0.5 mg colloidal silicon dioxide, about 0.01-0.3 mg magnesium stearate vegetable source, about 1-5 mg poly (methacrylic acid, ethyl acrylate) white, about 0.1-1 mg triethyl citrate and about 0.1-1 mg Opadry clear.

In certain embodiments, the weight of a pharmaceutical composition is about 11.248 mg and comprises about 1.5 mg Compound A, about 3.388 mg FAST FLO® 316, about 1.952 mg AVICEL® PH 101 or AVICEL® PH 102, about 0.226 mg sodium lauryl sulfate, about 0.226 mg AC DI SOL®, about 0.152 mg colloidal silicon dioxide, about 0.056 mg magnesium stearate vegetable source, about 2.836 mg poly(methacrylic acid, ethyl acrylate), about 0.284 mg triethyl citrate and about 0.628 mg Opadry clear.

6.1.3 Formulation C

In one embodiment, provided herein is a pharmaceutical composition comprising Compound A and one or more pharmaceutically acceptable excipients and carriers selected from diluents, surfactants, disintegrants, glidants, lubricants, polymers and plasticizers. In certain embodiments, the pharmaceutical compositions can be modifed-release-coated.

In certain embodiments, the diluents include, but are not limited to, lactose (e.g., lactose monohydrate (FAST FLO® 316)), cellulose (e.g., microcrystalline cellulose, such as AVICEL® PH 101 and AVICEL® PH 102). In one embodiment, the diluent is lactose. In another embodiment, the diluent is lactose monohydrate. In yet another embodiment, the diluent is FAST FLO® 316. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102).

In certain embodiments, the surfactants include, but are not limited to, organosulfate (e.g., sodium lauryl sulfate). In one embodiment, the surfactant is sodium lauryl sulfate.

In certain embodiments, the disintegrants include, but are not limited to, carboxymethyl cellulose (e.g., croscarmellose sodium, such as AC-DI-SOLO). In one embodiment, the disintegrant is carboxymethyl cellulose. In another embodiment, the disintegrant is croscarmellose sodium. In still another embodiment, the disintegrant is AC-DI-SOL®.

In certain embodiments, the glidants include, but are not limited to fumed silica (e.g., silicon oxide, such as colloidal silicon dioxide). In one embodiment, the gilant is silicon oxide. In another embodiment, the gilant is colloidal silicon dioxide.

In certain embodiments, the lubricants include, but are not limited to, magnesium stearate (e.g., magnesium stearate, vegetable source). In one embodiment, the lubricant is magnesium stearate. In another embodiment, the lubricant is magnesium stearate, vegetable source.

In certain embodiments, the polymers include, but are not limited to, poly(methyl acrylate, methyl methacrylate, methacrylic acid). In one embodiment, the polymer is poly (methyl acrylate, methyl methacrylate, methacrylic acid). In another embodiment, the polymer is poly(methyl acrylate, methyl methacrylate, methacrylic acid, 7:3:1).

In certain embodiments, the plasticizers include, but are not limited to and triethyl citrate. In one embodiment, the plasticizer is triethyl citrate.

In one embodiment, the modified-release coat is poly (methyl acrylate, methyl methacrylate, methacrylic acid). In another embodiment, the modified-release coat is poly(m-ethyl acrylate, methyl methacrylate, methacrylic acid, 7:3:1).

In certain embodiments, the coats include, but are not limited to, Opadry (e.g., Opadry clear). In one embodiment, the coat is Opadry. In another embodiment, the coat is Opadry clear.

In certain embodiments, provided herein are pharmaceutical compositions comprising Compound A and one or more pharmaceutically acceptable excipients or carriers, each independently selected from lactose, cellulose, organosulfate, carboxymethyl cellulose, fumed silica, magnesium stearate, poly(methyl acrylate, methyl methacrylate, methacrylic acid) and triethyl citrate. In certain embodiments, the pharmaceutical compositions are coated with Opadry. In certain embodiments, the pharmaceutical compositions are modifed-release-coated with poly(methyl acrylate, methyl methacrylate, methacrylic acid).

In certain embodiments, provided herein are pharmaceutical compositions comprising Compound A and one or more pharmaceutically acceptable excipients or carriers, each independently selected from lactose monohydrate, microcrystalline cellolose, sodium lauryl sulfate, croscarmellose sodium, silicon dioxide, magnesium stearate, poly(methyl acrylate, methyl methacrylate, methacrylic acid) and triethyl citrate. In certain embodiments, the pharmaceutical compositions are coated with Opadry. In certain embodiments, the pharmaceutical compositions are modifed-release-coated with poly(methyl acrylate, methyl methacrylate, methacrylic acid).

In certain embodiments, provided herein are pharmaceutical compositions comprising Compound A and one or more pharmaceutically acceptable excipients or carriers, each independently selected from FAST FLO® 316, AVICEL® PH 101, sodium lauryl sulfate, AC-DI-SOL®, colloidal silicon dioxide, magnesium stearate vegetable source, poly (methyl acrylate, methyl methacrylate, methacrylic acid) and triethyl citrate. In certain embodiments, the pharmaceutical compositions are coated with Opadry clear. In certain embodiments, the pharmaceutical compositions are modifed-release-coated with poly(methyl acrylate, methyl methacrylate, methacrylic acid, 7:3:1).

In one embodiment, provided herein is a pharmaceutical composition comprising Compound A, a diluent(s)/binder (s), a surfactant(s), a disintegratnt(s), a glidant(s), a lubricant (s), a polymer(s) and a plasticizer(s). In certain embodiments, the pharmaceutical compositions can be modifed-release-coated.

In one embodiment, provided herein is a pharmaceutical composition comprising Compound A, lactose and magnesium stearate.

In one embodiment, provided herein is a pharmaceutical composition comprising Compound A, lactose, cellulose and magnesium stearate.

In certain embodiments, provided herein are pharmaceutical compositions comprising Compound A, lactose monohydrate, microcrystalline cellulose, organosulfate, carboxymethyl cellulose, fumed silica and magnesium stearate.

In certain embodiments, provided herein are pharmaceutical compositions comprising Compound A, lactose monohydrate, microcrystalline cellulose, organosulfate, croscarmellose sodium, colloidal silicon dioxide, poly(methyl acrylate, methyl methacrylate, methacrylic acid), triethyl citrate, and magnesium stearate.

In certain embodiments, provided herein are pharmaceutical compositions comprising Compound A, FAST FLO 316®, AVICEL PH 102®, AC-DI-SOL®, poly(methyl acrylate, methyl methacrylate, methacrylic acid), triethyl citrate, and magnesium stearate.

In one embodiment, provided herein is a pharmaceutical composition comprising about 5-30% by weight of Compound A, about 30-70% by weight of diluent(s)/binder(s), about 1-5% by weight of surfactant(s), about 1-5% by weight of disintegrant(s), about 0.5-5% by weight of glidant(s), about 0.1-2% by weight of lubricant(s), about 1-10% by weight of polymer(s), about 0.1-5% by weight of plasticizer(s) and about 1-10% by weight of coat(s) (including modified-release coat(s)).

In one embodiment, provided herein is a pharmaceutical composition comprising about 18.14% by weight of Compound A, about 64.59% by weight of diluent(s)/binder(s), about 2.73% by weight of surfactant(s), about 2.73% by weight of disintegrant(s), about 1.84% by weight of glidant(s), about 0.68% by weight of lubricant(s), about 5.09% by weight of polymer(s), about 0.57% by weight of plasticizer(s) and about 3.63% by weight of coat(s) (including modified-release coat(s)).

In one embodiment, provided herein is a pharmaceutical composition comprising about 5-30% by weight of Compound A, about 15-50% by weight of lactose, about 5-40% by weight of cellulose, about 1-5% by weight of organosulfate, about 1-5% by weight of carboxymethyl cellulose, about 0.5-5% by weight of fumed silica, about 0.1-2% by weight of magnesium stearate, about 1-10% by weight of poly(methyl acrylate, methyl methacrylate, methacrylic acid), about 0.1-5% by weight of triethyl citrate and about 1-10% by weight of Opadry.

In one embodiment, provided herein is a pharmaceutical composition comprising about 5-30% by weight of Compound A, about 15-50% by weight of lactose, about 5-40% by weight of cellulose, about 0-10% by weight of organosulfate, about 1-5% by weight of carboxymethyl cellulose, about 0.5-5% by weight of fumed silica, about 0.1-2% by weight of magnesium stearate, about 1-25% by weight of poly(methyl acrylate, methyl methacrylate, methacrylic acid), about 0.1-5% by weight of triethyl citrate and about 1-10% by weight of Opadry.

In one embodiment, provided herein is a pharmaceutical composition comprising about 18% by weight of Compound A, about 41% by weight of lactose, about 24% by weight of cellulose, about 3% by weight of organosulfate, about 3% by weight of carboxymethyl cellulose, about 2% by weight of fumed silica, about 1% by weight of magnesium stearate, about 5% by weight of poly(methyl acrylate, methyl methacrylate, methacrylic acid), about 1% by weight of triethyl citrate and about 4% by weight of Opadry.

In one embodiment, provided herein is a pharmaceutical composition comprising about 18.14% by weight of Compound A, about 40.98% by weight of lactose, about 23.61% by weight of cellulose, about 2.73% by weight of organosulfate, about 2.73% by weight of carboxymethyl cellulose, about 1.84% by weight of fumed silica, about 0.68% by weight of magnesium stearate, about 5.09% by weight of poly(methyl acrylate, methyl methacrylate, methacrylic acid), about 0.57% by weight of triethyl citrate and about 3.63% by weight of Opadry.

In one embodiment, provided herein is a pharmaceutical composition comprising about 5-30% by weight of Compound A, about 15-50% by weight of lactose monohydrate, about 5-40% by weight of microcrystalline cellulose, about 1-5% by weight of sodium lauryl sulfate, about 1-5% by weight of croscarmellose sodium, about 0.5-5% by weight of colloidal silicon dioxide, about 0.1-2% by weight of magnesium stearate, about 1-10% by weight of poly(methyl acrylate, methyl methacrylate, methacrylic acid), about 0.1-5% by weight of triethyl citrate and about 1-10% by weight of Opadry.

In one embodiment, provided herein is a pharmaceutical composition comprising about 18% by weight of Compound A, about 41% by weight of lactose monohydrate, about 24% by weight of microcrystalline cellulose, about 3% by weight of sodium lauryl sulfate, about 3% by weight of croscarmellose sodium, about 2% by weight of colloidal silicon dioxide, about 1% by weight of magnesium stearate, about 5% by weight of poly(methyl acrylate, methyl methacrylate, methacrylic acid), about 1% by weight of triethyl citrate and about 4% by weight of Opadry.

In one embodiment, provided herein is a pharmaceutical composition comprising about 18.14% by weight of Compound A, about 40.98% by weight of lactose monohydrate, about 23.61% by weight of microcrystalline cellulose, about 2.73% by weight of sodium lauryl sulfate, about 2.73% by weight of croscarmellose sodium, about 1.84% by weight of colloidal silicon dioxide, about 0.68% by weight of magnesium stearate, about 5.09% by weight of poly(methyl acrylate, methyl methacrylate, methacrylic acid), about 0.57% by weight of triethyl citrate and about 3.63% by weight of Opadry.

In one embodiment, provided herein is a pharmaceutical composition comprising about 5-30% by weight of Compound A, about 15-50% by weight of FAST FLO® 316, about 5-40% by weight of AVICEL® PH 101 or AVICEL® PH 102, about 1-5% by weight of sodium lauryl sulfate, about 1-5% by weight of AC DI SOLO, about 0.5-5% by weight of colloidal silicon dioxide, about 0.1-2% by weight of magnesium stearate vegetable source, about 1-10% by weight of poly(methyl acrylate, methyl methacrylate, methacrylic acid), about 0.1-5% by weight of triethyl citrate and about 1-10% by weight of Opadry clear.

In one embodiment, provided herein is a pharmaceutical composition comprising about 18.14% by weight of Compound A, about 40.98% by weight of FAST FLO® 316, about 23.61% by weight of AVICEL® PH 101 or AVICEL® PH 102, about 2.73% by weight of sodium lauryl sulfate, about 2.73% by weight of AC-DI-SOL®, about 1.84% by weight of colloidal silicon dioxide, about 0.68% by weight of magnesium stearate vegetable source, about 5.09% by weight of poly(methyl acrylate, methyl methacrylate, methacrylic acid), about 0.57% by weight of triethyl citrate and about 3.63% by weight of Opadry clear.

In certain embodiments, the weight of a pharmaceutical composition is about 5-20 mg. In one embodiment, the pharmaceutical composition comprises about 0.5-3 mg Compound A, about 2-10 mg diluent(s)/binder(s), about 0.1-1 mg surfactant(s), about 0.1-1 mg disintegrant(s), about 0.05-0.5 mg glidant(s), about 0.01-0.3 mg lubricant(s), about 0.1-5 mg polymer(s), about 0.01-1 mg plasticizer(s) and about 0.1-1 mg coat(s) (including modified-release coat(s)).

In certain embodiments, the weight of a pharmaceutical composition is about 8.268 mg. In one embodiment, the pharmaceutical composition comprises about 1.5 mg Compound A, about 5.34 mg diluent(s)/binder(s), about 0.226 mg surfactant(s), about 0.226 mg disintegrant(s), about 0.152 mg glidant(s), about 0.056 mg lubricant(s), about 0.421 mg polymer(s), about 0.047 mg plasticizer(s) and about 0.628 mg coat(s) (including modified-release coat(s)).

In certain embodiments, the weight of a pharmaceutical composition is about 5-20 mg and comprises about 0.5-3 mg Compound A, about 1-5 mg lactose, about 1-5 mg cellulose, about 0.1-1 mg organosulfate, about 0.1-1 mg carboxymethyl cellulose, about 0.05-0.5 mg fumed silica, about 0.01-

0.3 mg magnesium stearate, about 0.1-5 mg poly(methyl acrylate, methyl methacrylate, methacrylic acid), about 0.01-1 mg triethyl citrate and about 0.1-1 mg Opadry.

In certain embodiments, the weight of a pharmaceutical composition is about 8.268 mg and comprises about 1.5 mg Compound A, about 3.388 mg lactose, about 1.952 mg cellulose, about 0.226 mg organosulfate, about 0.226 mg carboxymethyl cellulose, about 0.152 mg fumed silica, about 0.056 mg magnesium stearate, about 0.421 mg poly (methyl acrylate, methyl methacrylate, methacrylic acid), about 0.047 mg triethyl citrate and about 0.300 mg Opadry.

In certain embodiments, the weight of a pharmaceutical composition is about 5-20 mg and comprises about 0.5-3 mg Compound A, about 1-5 mg lactose monohydrate, about 1-5 mg microcrystalline cellulose, about 0.1-1 mg sodium lauryl sulfate, about 0.1-1 mg croscarmellose sodium, about 0.05-0.5 mg colloidal silicon dioxide, about 0.01-0.3 mg magnesium stearate, about 0.1-5 mg poly(methyl acrylate, methyl methacrylate, methacrylic acid), about 0.01-1 mg triethyl citrate and about 0.1-1 mg Opadry.

In certain embodiments, the weight of a pharmaceutical composition is about 8.268 mg and comprises about 1.5 mg Compound A, about 3.388 mg lactose monohydrate, about 1.952 mg microcrystalline cellulose, about 0.226 mg sodium lauryl sulfate, about 0.226 mg croscarmellose sodium, about 0.152 mg colloidal silicon dioxide, about 0.056 mg magnesium stearate, about 0.421 mg poly(methyl acrylate, methyl methacrylate, methacrylic acid), about 0.047 mg triethyl citrate and about 0.300 mg Opadry.

In certain embodiments, the weight of a pharmaceutical composition is about 5-20 mg and comprises about 0.5-3 mg Compound A, about 1-5 mg FAST FLO® 316, about 1-5 mg AVICEL® PH 101 or AVICEL® PH 102, about 0.1-1 mg sodium lauryl sulfate, about 0.1-1 mg AC DI SOL®, about 0.05-0.5 mg colloidal silicon dioxide, about 0.01-0.3 mg magnesium stearate vegetable source, about 0.1-5 mg poly (methyl acrylate, methyl methacrylate, methacrylic acid), about 0.01-1 mg triethyl citrate and about 0.1-1 mg Opadry clear.

In certain embodiments, the weight of a pharmaceutical composition is about 8.268 mg and comprises about 1.5 mg Compound A, about 3.388 mg FAST FLO® 316, about 1.952 mg AVICEL® PH 101 or AVICEL® PH 102, about 0.226 mg sodium lauryl sulfate, about 0.226 mg AC DI SOL®, about 0.152 mg colloidal silicon dioxide, about 0.056 mg magnesium stearate vegetable source, about 0.421 mg poly(methyl acrylate, methyl methacrylate, methacrylic acid), about 0.047 mg triethyl citrate and about 0.300 mg Opadry clear.

6.1.4 Formulation D

In one embodiment, provided herein is a pharmaceutical composition comprising Compound A and one or more pharmaceutically acceptable excipients and carriers selected from diluents, surfactants, glidants, lubricants, polymers and pore formers. In certain embodiments, the pharmaceutical compositions can be modifed-release-coated.

In certain embodiments, the diluents include, but are not limited to, starch (e.g., pregelatinized starch), cellulose (e.g., microcrystalline cellulose, such as AVICEL® PH 101 and AVICEL® PH 102). In one embodiment, the diluent is starch. In another embodiment, the diluent is pregelatinized starch. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, organosulfate (e.g., sodium lauryl sulfate). In one embodiment, the surfactant is sodium lauryl sulfate.

In certain embodiments, the glidants include, but are not limited to fumed silica (e.g., silicon oxide, such as colloidal silicon dioxide). In one embodiment, the gilant is silicon oxide. In another embodiment, the gilant is colloidal silicon dioxide.

In certain embodiments, the lubricants include, but are not limited to, magnesium stearate (e.g., magnesium stearate, vegetable source). In one embodiment, the lubricant is magnesium stearate. In another embodiment, the lubricant is magnesium stearate, vegetable source.

In certain embodiments, the polymers include, but are not limited to, polyethylene oxide and ethylcellulose (e.g., ethylcellulose clear). In one embodiments, the polymer is polyethylene oxide. In another embodiments, the polymer is ethylcellulose. In another embodiments, the polymer is ethylcellulose clear.

In certain embodiments, the pore formers include, but are not limited to, Opadry (e.g., Opadry clear). In one embodiment, the pore former is Opadry. In another embodiment, the pore former is Opadry clear.

In certain embodiments, the coats include, but are not limited to, Opadry (e.g., Opadry clear). In one embodiment, the coat is Opadry. In one embodiment, the coat is Opadry. In another embodiment, the coat is Opadry clear.

In one embodiment, the modified-release coat is ethylcellulose. In another embodiment, the modified-release coat is ethylcellulose clear.

In certain embodiments, provided herein are pharmaceutical compositions comprising Compound A and one or more pharmaceutically acceptable excipients or carriers, each independently selected from starch, cellulose, organosulfate, fumed silica, magnesium stearate, polyethylene oxide and ethylcellulose. In certain embodiments, the pharmaceutical compositions are coated with Opadry. In certain embodiments, the pharmaceutical compositions are modifed-release-coated with ethylcellulose.

In certain embodiments, provided herein are pharmaceutical compositions comprising Compound A and one or more pharmaceutically acceptable excipients or carriers, each independently selected from pregelatinized starch, microcrystalline cellolose, sodium lauryl sulfate, silicon dioxide, magnesium stearate, polyethylene oxide and ethylcellulose. In certain embodiments, the pharmaceutical compositions are coated with Opadry. In certain embodiments, the pharmaceutical compositions are modifed-release-coated with ethylcellulose.

In certain embodiments, provided herein are pharmaceutical compositions comprising Compound A and one or more pharmaceutically acceptable excipients or carriers, each independently selected from pregelatinized starch, AVICEL® PH 101, sodium lauryl sulfate, colloidal silicon dioxide, magnesium stearate vegetable source, polyethylene oxide and ethylcellulose clear. In certain embodiments, the pharmaceutical compositions are coated with Opadry clear. In certain embodiments, the pharmaceutical compositions are modifed-release-coated with ethylcellulose clear.

In one embodiment, provided herein is a pharmaceutical composition comprising Compound A, a diluent(s)/binder (s), a surfactant(s), a glidant(s), a lubricant(s), a polymer(s), a pore former(s). In certain embodiments, the pharmaceutical compositions can be modifed-release-coated.

In one embodiment, provided herein is a pharmaceutical composition comprising Compound A, starch and magnesium stearate.

In one embodiment, provided herein is a pharmaceutical composition comprising Compound A, starch, cellulose and magnesium stearate.

In certain embodiments, provided herein are pharmaceutical compositions comprising Compound A, pregelatinized starch, microcrystalline cellulose, organosulfate, fumed silica and magnesium stearate.

In certain embodiments, provided herein are pharmaceutical compositions comprising Compound A, pregelatinized starch, microcrystalline cellulose, organosulfate, colloidal silicon dioxide, polyethylene oxide, ethylcellulose and magnesium stearate. In certain embodiments, the pharmaceutical compositions are coated with Opadry. In certain embodiments, the pharmaceutical compositions are modifed-release-coated with ethylcellulose.

In certain embodiments, provided herein are pharmaceutical compositions comprising Compound A, pregelatinized starch, AVICEL PH 102®, sodium lauryl sulfate, colloidal silicon dioxide, polyethylene oxide, ethylcellulose clear and magnesium stearate. In certain embodiments, the pharmaceutical compositions are coated with Opadry clear. In certain embodiments, the pharmaceutical compositions are modifed-release-coated with ethylcellulose clear.

In one embodiment, provided herein is a pharmaceutical composition comprising about 5-30% by weight of Compound A, about 30-70% by weight of diluent(s)/binder(s), about 1-5% by weight of surfactant(s), about 0.5-5% by weight of glidant(s), about 0.1-2% by weight of lubricant(s), about 20-60% by weight of polymer(s), about 1-10% by weight of pore former(s) and about 1-10% by weight of coat(s) (including modified-release coat(s)).

In one embodiment, provided herein is a pharmaceutical composition comprising about 17.25% by weight of Compound A, about 38.48% by weight of diluent(s)/binder(s), about 2.60% by weight of surfactant(s), about 1.72% by weight of glidant(s), about 0.44% by weight of lubricant(s), about 32.43% by weight of polymer(s), about 2.91% by weight of pore former(s) and about 6.37% by weight of coat(s) (including modified-release coat(s)).

In one embodiment, provided herein is a pharmaceutical composition comprising about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In one embodiment, provided herein is a pharmaceutical composition comprising about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 0-10% by weight of ethylcellulose, about 1-10% by weight of Opadry as pore former and about 1-10% by weight of Opadry as coat.

In one embodiment, provided herein is a pharmaceutical composition comprising about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In one embodiment, provided herein is a pharmaceutical composition comprising about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 0-20% by weight of ethylcellulose, about 0-20% by weight of Opadry as pore former and about 1-10% by weight of Opadry as coat.

In one embodiment, provided herein is a pharmaceutical composition comprising about 17% by weight of Compound A, about 13% by weight of starch, about 26% by weight of cellulose, about 3% by weight of organosulfate, about 2% by weight of fumed silica, about 0.5% by weight of magnesium stearate, about 26% by weight of polyethylene oxide, about 6% by weight of ethylcellulose, about 3% by weight of Opadry as pore former and about 6% by weight of Opadry as coat.

In one embodiment, provided herein is a pharmaceutical composition comprising about 17.25% by weight of Compound A, about 12.97% by weight of starch, about 25.51% by weight of cellulose, about 2.60% by weight of organosulfate, about 1.72% by weight of fumed silica, about 0.44% by weight of magnesium stearate, about 25.94% by weight of polyethylene oxide, about 6.49% by weight of ethylcellulose, about 2.91% by weight of Opadry as pore former and about 6.37% by weight of Opadry as coat.

In one embodiment, provided herein is a pharmaceutical composition comprising about 5-30% by weight of Compound A, about 5-50% by weight of pregelatinized starch, about 5-40% by weight of microcrystalline cellulose, about 1-5% by weight of sodium lauryl sulfate, about 0.5-5% by weight of colloidal silicon dioxide, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In one embodiment, provided herein is a pharmaceutical composition comprising about 5-30% by weight of Compound A, about 5-50% by weight of pregelatinized starch, about 5-40% by weight of microcrystalline cellulose, about 1-5% by weight of sodium lauryl sulfate, about 0.5-5% by weight of colloidal silicon dioxide, about 0.1-2% by weight of magnesium stearate, about 10-50% by weight of polyethylene oxide, about 0-10% by weight of ethylcellulose, about 1-10% by weight of Opadry as pore former and about 1-10% by weight of Opadry as coat.

In one embodiment, provided herein is a pharmaceutical composition comprising about 17% by weight of Compound A, about 13% by weight of pregelatinized starch, about 26% by weight of microcrystalline cellulose, about 3% by weight of sodium lauryl sulfate, about 2% by weight of colloidal silicon dioxide, about 0.5% by weight of magnesium stearate, about 26% by weight of polyethylene oxide, about 6% by weight of ethylcellulose, about 3% by weight of Opadry as pore former and about 6% by weight of Opadry as coat.

In one embodiment, provided herein is a pharmaceutical composition comprising about 17.25% by weight of Compound A, about 12.97% by weight of pregelatinized starch, about 25.51% by weight of microcrystalline cellulose, about 2.60% by weight of sodium lauryl sulfate, about 1.72% by weight of colloidal silicon dioxide, about 0.44% by weight of magnesium stearate, about 25.94% by weight of polyethylene oxide, about 6.49% by weight of ethylcellulose, about 2.91% by weight of Opadry as pore former and about 6.37% by weight of Opadry as coat.

In one embodiment, provided herein is a pharmaceutical composition comprising about 5-30% by weight of Compound A, about 5-50% by weight of pregelatinized starch, about 5-40% by weight of AVICEL® PH 101 or AVICEL® PH 102, about 1-5% by weight of sodium lauryl sulfate, about 0.5-5% by weight of colloidal silicon dioxide, about 0.1-2% by weight of magnesium stearate, about 10-50% by weight of polyethylene oxide, about 1-10% by weight of ethylcellulose clear, about 1-10% by weight of Opadry clear as pore former and about 1-10% by weight of Opadry clear as coat.

In one embodiment, provided herein is a pharmaceutical composition comprising about 5-30% by weight of Compound A, about 5-50% by weight of pregelatinized starch, about 5-40% by weight of AVICEL® PH 101 or AVICEL® PH 102, about 1-5% by weight of sodium lauryl sulfate, about 0.5-5% by weight of colloidal silicon dioxide, about 0.1-2% by weight of magnesium stearate, about 10-50% by weight of polyethylene oxide, about 0-10% by weight of ethylcellulose clear, about 1-10% by weight of Opadry clear as pore former and about 1-10% by weight of Opadry clear as coat.

In one embodiment, provided herein is a pharmaceutical composition comprising about 17.25% by weight of Compound A, about 12.97% by weight of pregelatinized starch, about 25.51% by weight of AVICEL® PH 101 or AVICEL® PH 102, about 2.60% by weight of sodium lauryl sulfate, about 1.72% by weight of colloidal silicon dioxide, about 0.44% by weight of magnesium stearate, about 25.94% by weight of polyethylene oxide, about 6.49% by weight of ethylcellulose clear, about 2.91% by weight of Opadry clear as pore former and about 6.37% by weight of Opadry clear as coat.

In certain embodiments, the weight of a pharmaceutical composition is about 5-20 mg. In one embodiment, the pharmaceutical composition comprises about 0.5-3 mg Compound A, about 2-10 mg diluent(s)/binder(s), about 0.1-1 mg surfactant(s), about 0.05-0.5 mg glidant(s), about 0.01-0.3 mg lubricant(s), about 0.1-5 mg polymer(s), about 0.1-1 mg pore former(s) and about 0.1-1 mg coat(s) (including modified-release coat(s)).

In certain embodiments, the weight of a pharmaceutical composition is about 8.696 mg. In one embodiment, the pharmaceutical composition comprises about 1.5 mg Compound A, about 3.346 mg diluent(s)/binder(s), about 0.226 mg surfactant(s), about 0.150 mg glidant(s), about 0.038 mg lubricant(s), about 2.82 mg polymer(s), about 0.253 mg pore former(s) and about 0.554 mg coat(s) (including modified-release coat(s)).

In certain embodiments, the weight of a pharmaceutical composition is about 5-20 mg and comprises about 0.5-3 mg Compound A, about 1-5 mg starch, about 1-5 mg cellulose, about 0.1-1 mg organosulfate, about 0.05-0.5 mg fumed silica, about 0.01-0.3 mg magnesium stearate, about 0.1-5 mg polyethylene oxide, about 0.1-1 mg ethylcellulose, about 0.1-1 mg Opadry as pore former and about 0.1-1 mg Opadry as coat.

In certain embodiments, the weight of a pharmaceutical composition is about 8.696 mg and comprises about 1.5 mg Compound A, about 1.128 mg starch, about 2.218 mg cellulose, about 0.226 mg organosulfate, about 0.150 mg fumed silica, about 0.038 mg magnesium stearate, about 2.256 mg polyethylene oxide, about 0.564 mg ethylcellulose, about 0.253 mg Opadry as pore former and about 0.554 mg Opadry as coat.

In certain embodiments, the weight of a pharmaceutical composition is about 5-20 mg and comprises about 0.5-3 mg Compound A, about 1-5 mg pregelatinized starch, about 1-5 mg microcrystalline cellulose, about 0.1-1 mg sodium lauryl sulfate, about 0.05-0.5 mg colloidal silicon dioxide, about 0.01-0.3 mg magnesium stearate, about 0.1-0.3 mg polyethylene oxide, about 0.1-1 mg ethylcellulose, about 0.1-1 mg Opadry as pore former and about 0.1-1 mg Opadry as coat.

In certain embodiments, the weight of a pharmaceutical composition is about 8.696 mg and comprises about 1.5 mg Compound A, about 1.128 mg pregelatinized starch, about 2.218 mg microcrystalline cellulose, about 0.226 mg sodium lauryl sulfate, about 0.150 mg colloidal silicon dioxide, about 0.038 mg magnesium stearate, about 2.256 mg polyethylene oxide, about 0.564 mg ethylcellulose, about 0.253 mg Opadry as pore former and about 0.554 mg Opadry as coat.

In certain embodiments, the weight of a pharmaceutical composition is about 5-20 mg and comprises about 0.5-3 mg Compound A, about 1-5 mg pregelatinized starch, about 1-5 mg AVICEL® PH 101 or AVICEL® PH 102, about 0.1-1 mg sodium lauryl sulfate, about 0.05-0.5 mg colloidal silicon dioxide, about 0.01-0.3 mg magnesium stearate, about 0.1-5 mg polyethylene oxide, about 0.1-1 mg ethylcellulose clear, about 0.1-1 mg Opadry clear as pore former and about 0.1-1 mg Opadry clear as coat.

In certain embodiments, the weight of a pharmaceutical composition is about 8.696 mg and comprises about 1.5 mg Compound A, about 1.128 mg pregelatinized starch, about 2.218 mg AVICEL® PH 101 or AVICEL® PH 102, about 0.226 mg sodium lauryl sulfate, about 0.150 mg colloidal silicon dioxide, about 0.038 mg magnesium stearate, about 2.256 mg polyethylene oxide, about 0.564 mg ethylcellulose clear, about 0.253 mg Opadry clear as pore former and about 0.554 mg Opadry clear as coat.

6.1.5 Formulation E

In one embodiment, provided herein is a pharmaceutical composition comprising Formulation D.

In one embodiment, provided herein is a pharmaceutical composition comprising about 80-100% by weight of Formulation D.

In one embodiment, provided herein is a pharmaceutical composition comprising about 100% by weight of Formulation D.

In certain embodiments, provided herein are pharmaceutical compositions comprising dosage forms of Formulation D. In certain embodiments, provided herein are pharmaceutical compositions weighing about 200-800 mg. In certain embodiments, provided herein are pharmaceutical compositions comprising about 200-800 mg Formulation D.

In certain embodiments, provided herein are pharmaceutical compositions weighing about 434 mg. In certain embodiments, provided herein are pharmaceutical compositions comprising about 434 mg Formulation D.

In certain embodiments, provided herein are pharmaceutical compositions comprising about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 80-100% by weight of a component dosage form, wherein the component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation E is a multiparticulate formulation comprising discrete units (e.g., multiparticulates, minitabs or minitablets) of Formulation D.

6.1.6 Formulation F

In one embodiment, provided herein is a pharmaceutical composition comprising Formulations A and D.

In one embodiment, provided herein is a pharmaceutical composition comprising about 10-30% by weight of Formulation A, and about 70-90% by weight of Formulation D.

In one embodiment, provided herein is a pharmaceutical composition comprising about 5-50% by weight of Formulation A, and about 50-95% by weight of Formulation D.

In one embodiment, provided herein is a pharmaceutical composition comprising about 18.35% by weight of Formulation A, and about 81.65% by weight of Formulation D.

In certain embodiments, provided herein are pharmaceutical compositions weighing about 200-1000 mg. In one embodiment, the pharmaceutical composition comprises about 50-100 mg Formulation A, and about 250-500 mg Formulation D.

In certain embodiments, provided herein are pharmaceutical compositions weighing about 425 mg. In one embodiment, the pharmaceutical composition comprises about 78 mg Formulation A and about 347 mg Formulation D.

In certain embodiments, provided herein are pharmaceutical compositions comprising about 10-30% by weight of a first component dosage form and about 70-90% by weight of a second component dosage form, wherein the first component dosage form comprises about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 10-40% by weight of a first component dosage form and about 60-90% by weight of a second component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, provided herein are pharmaceutical compositions comprising about 5-50% by weight of a first component dosage form and about 50-95% by weight of a second component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, provided herein are pharmaceutical compositions comprising about 5-50% by weight of a first component dosage form and about 50-95% by weight of a second component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation F is a multiparticulate formulation comprising discrete units (e.g., multiparticulates, minitabs or minitablets) of Formulations A and D.

6.1.7 Formulation G

In one embodiment, provided herein is a pharmaceutical composition comprising Formulations A, B and C.

In one embodiment, provided herein is a pharmaceutical composition comprising about 20-60% by weight of Formulation A, about 10-30% by weight of Formulation B and about 30-60% by weight of Formulation C.

In one embodiment, provided herein is a pharmaceutical composition comprising about 34.03% by weight of Formulation A, about 20.98% by weight of Formulation B and about 44.99% by weight of Formulation C.

In certain embodiments, provided herein are pharmaceutical compositions weighing about 200-800 mg. In one embodiment, the pharmaceutical composition comprises about 100-200 mg Formulation A, about 50-150 mg Formulation B and about 100-300 mg Formulation C.

In certain embodiments, provided herein are pharmaceutical compositions weighing about 429 mg. In one embodiment, the pharmaceutical composition comprises about 146 mg Formulation A, about 90 mg Formulation B and about 193 mg Formulation C.

In certain embodiments, provided herein are pharmaceutical compositions comprising about 20-60% by weight of a first component dosage form, about 10-30% by weight of a second component dosage form and about 30-60% by weight of a third component dosage form, wherein the first component dosage form comprises about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry; wherein the second component dosage form comprises about 5-30% by weight of Compound A, about 15-45% by weight of lactose, about 5-30% by weight of cellulose, about 1-5% by weight of organosulfate, about 1-5% by weight of carboxymethyl cellulose, about 0.5-5% by weight of fumed silica, about 0.1-2% by weight of magnesium stearate, about 10-50% by weight of poly(methacrylic acid, ethyl acrylate), about 1-10% by weight of triethyl citrate and about 1-10% by weight of Opadry; and wherein the third component dosage form comprises about 5-30% by weight of Compound A, about 15-50% by weight of lactose, about 5-40% by weight of cellulose, about 1-5% by weight of organosulfate, about 1-5% by weight of carboxymethyl cellulose, about 0.5-5% by weight of fumed silica, about 0.1-2% by weight of magnesium stearate, about 1-10% by weight of poly(methyl acrylate, methyl methacrylate, methacrylic acid), about 0.1-5% by weight of triethyl citrate and about 1-10% by weight of Opadry.

In certain embodiments, provided herein are pharmaceutical compositions comprising about 10-50% by weight of a first component dosage form, about 10-30% by weight of a second component dosage form and about 30-60% by weight of a third component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; wherein the second component dosage form comprises about 5-30% by weight of Compound A, about 15-45% by weight of lactose, about 5-30% by weight of cellulose, about 0-10% by weight of organosulfate, about 1-5% by weight of carboxymethyl cellulose, about 0.5-5% by weight of fumed silica, about 0.1-2% by weight of magnesium stearate, about 5-50% by weight of poly(methacrylic acid, ethyl acrylate), about 1-10% by weight of triethyl citrate and about 1-10% by weight of Opadry; and wherein the third component dosage form comprises about 5-30% by weight of Compound A, about 15-50% by weight of lactose, about 5-40% by weight of cellulose, about 0-10% by weight of organosulfate, about 1-5% by weight of carboxymethyl cellulose, about 0.5-5% by weight of fumed silica, about 0.1-2% by weight of magnesium stearate, about 1-25% by weight of poly(methyl acrylate, methyl methacrylate, methacrylic acid), about 0.1-5% by weight of triethyl citrate and about 1-10% by weight of Opadry.

In certain embodiments, the pharmaceutical compositions are capsule dosage forms.

In one embodiment, provided herein is a capsule dosage form suitable for administration in a size 4 or larger capsule.

In one embodiment, Formulation G is a multiparticulate formulation comprising discrete units (e.g., multiparticulates, minitabs or minitablets) of Formulations A, B and C.

Figure 6:
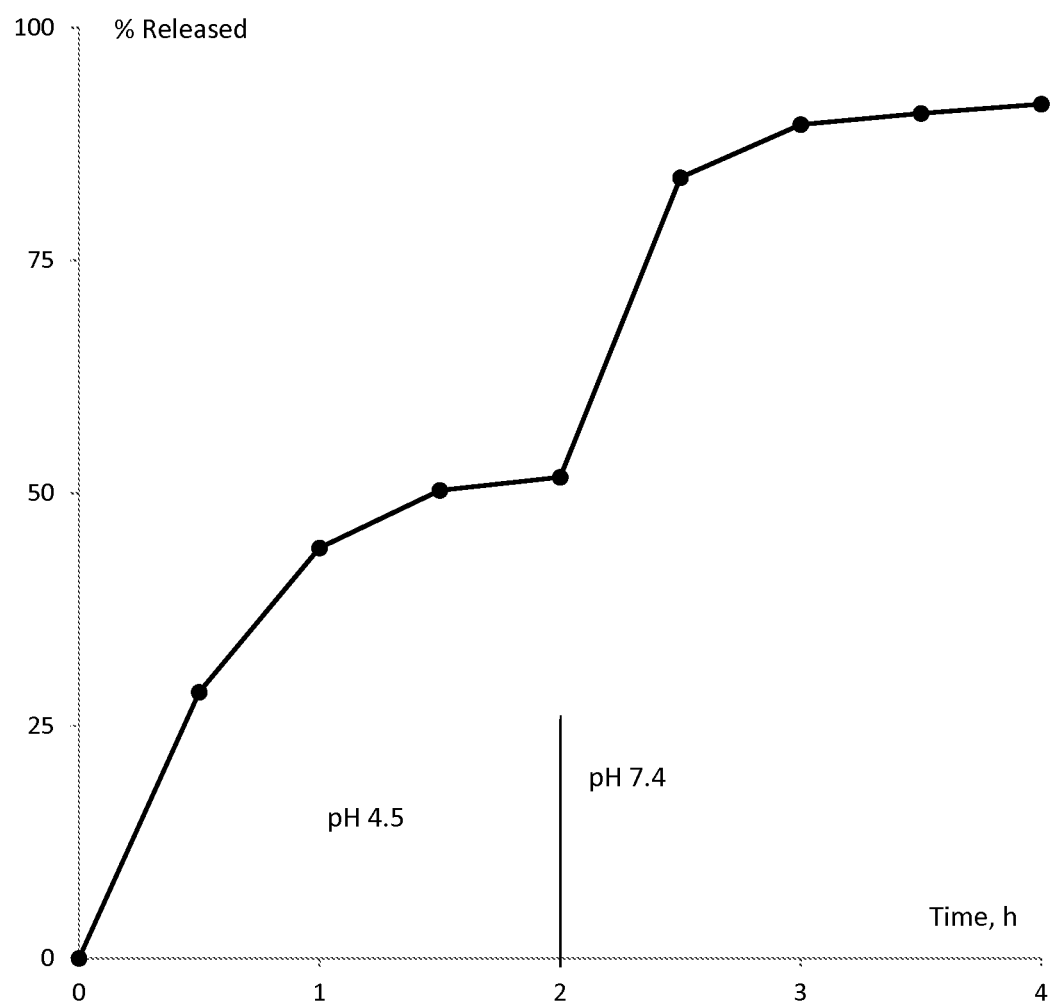
FIG. 6: Dissolution profile for Formulation G.

In certain embodiments, the pharmaceutical compositions comprising Formulation G provide pH-dependent release of Compound A (see, e.g., FIG. 6).

Without being limited by theory, the amount of each component dosage form (e.g., Formulations A, B and C) that comprises pharmaceutical compositions of Formulation G can dictate the pH-release profile.

6.1.8 Formulation H

In one embodiment, provided herein is a pharmaceutical composition comprising Formulations A, C and D.

In one embodiment, provided herein is a pharmaceutical composition comprising about 10-50% by weight of Formulation A, about 5-30% by weight of Formulation C and about 50-80% by weight of Formulation D.

In one embodiment, provided herein is a pharmaceutical composition comprising about 24.82% by weight of Formulation A, about 13.13% by weight of Formulation C and about 62.05% by weight of Formulation D.

In certain embodiments, provided herein are pharmaceutical compositions weighing about 200-800 mg. In one embodiment, the pharmaceutical composition comprises about 50-150 mg Formulation A, about 10-100 mg Formulation C and about 100-500 mg Formulation D.

In certain embodiments, provided herein are pharmaceutical compositions weighing about 419 mg. In one embodiment, the pharmaceutical composition comprises about 104 mg Formulation A, about 55 mg Formulation C and about 260 mg Formulation D.

In certain embodiments, provided herein are pharmaceutical compositions comprising about 20-60% by weight of a first component dosage form, about 10-30% by weight of a second component dosage form and about 30-60% by weight of a third component dosage form, wherein the first component dosage form comprises about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry; wherein the second component dosage form comprises about 5-30% by weight of Compound A, about 15-50% by weight of lactose, about 5-40% by weight of cellulose, about 1-5% by weight of organosulfate, about 1-5% by weight of carboxymethyl cellulose, about 0.5-5% by weight of fumed silica, about 0.1-2% by weight of magnesium stearate, about 1-10% by weight of poly(methyl acrylate, methyl methacrylate, methacrylic acid), about 0.1-5% by weight of triethyl citrate and about 1-10% by weight of Opadry; and wherein the third component dosage form comprises about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 0-50% by weight of a first component dosage form, about 5-30% by weight of a second component dosage form and about 30-85% by weight of a third component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; wherein the second component dosage form comprises about 5-30% by weight of Compound A, about 15-50% by weight of lactose, about 5-40% by weight of cellulose, about 0-10% by weight of organosulfate, about 1-5% by weight of carboxymethyl cellulose, about 0.5-5% by weight of fumed silica, about 0.1-2% by weight of magnesium stearate, about 1-25% by weight of poly(methyl acrylate, methyl methacrylate, methacrylic acid), about 0.1-5% by weight of triethyl citrate and about 1-10% by weight of Opadry; and wherein the third component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation H is a multiparticulate formulation comprising discrete units (e.g., multiparticulates, minitabs or minitablets) of Formulations A, C and D.

Figure 7:
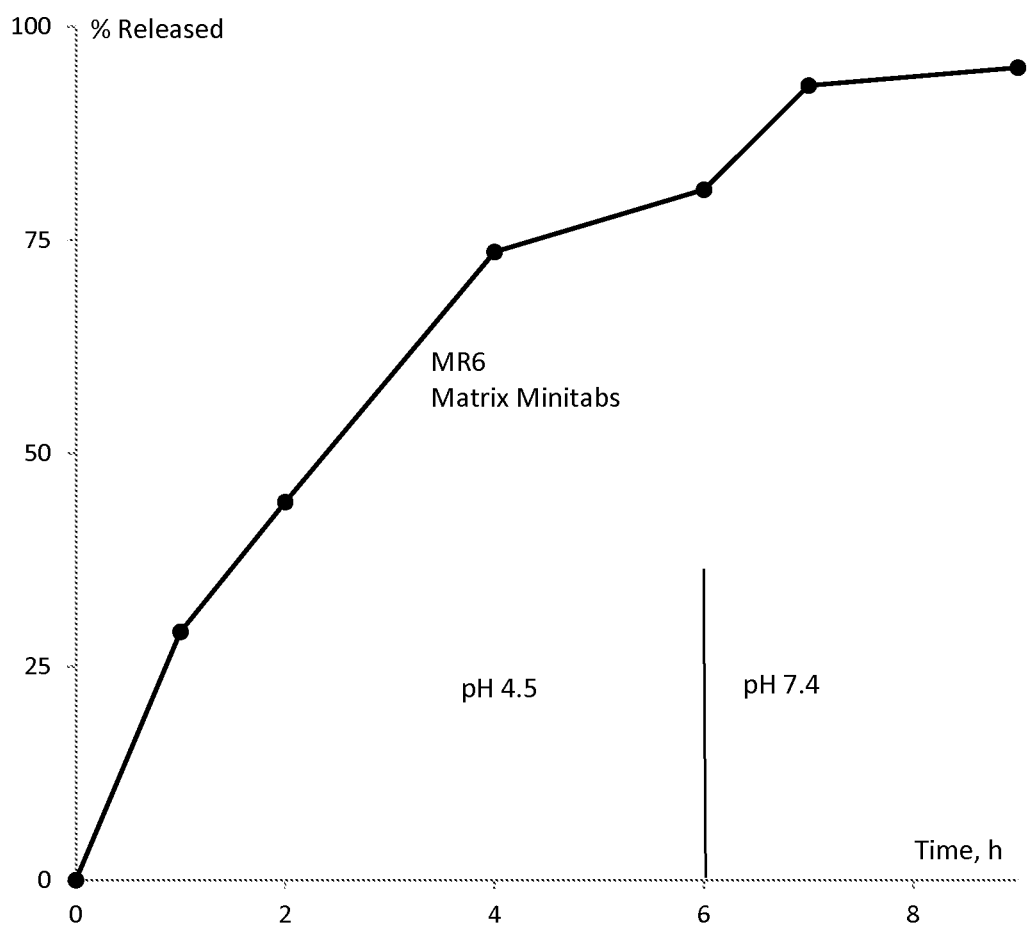
FIG. 7: Dissolution profile for Formulation H.

In certain embodiments, the pharmaceutical compositions comprising Formulation H provide pH-dependent release of Compound A (see, e.g., FIG. 7).

Without being limited by theory, the amount of each component dosage form (e.g., Formulations A, C and D) that comprises pharmaceutical compositions of Formulation H can dictate the pH-release profile.

6.1.9 Formulation I

In one embodiment, provided herein is a pharmaceutical composition comprising Compound A and one or more pharmaceutically acceptable excipients and carriers selected from diluents, surfactants, glidants, lubricants and polymers.

In certain embodiments, the diluents include, but are not limited to, starch (e.g., pregelatinized starch), cellulose (e.g., microcrystalline cellulose, such as AVICEL® PH 101 and AVICEL® PH 102). In one embodiment, the diluent is starch. In another embodiment, the diluent is pregelatinized starch. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102.

In certain embodiments, the surfactants include, but are not limited to, organosulfate (e.g., sodium lauryl sulfate). In one embodiment, the surfactant is sodium lauryl sulfate.

In certain embodiments, the glidants include, but are not limited to fumed silica (e.g., silicon oxide, such as colloidal silicon dioxide). In one embodiment, the gilant is silicon oxide. In another embodiment, the gilant is colloidal silicon dioxide.

In certain embodiments, the lubricants include, but are not limited to, magnesium stearate (e.g., magnesium stearate, vegetable source). In one embodiment, the lubricant is magnesium stearate. In another embodiment, the lubricant is magnesium stearate, vegetable source.

In another embodiment, provided herein is a pharmaceutical composition comprising Compound A and one or more pharmaceutically acceptable excipients or carriers, each independently selected from starch, cellulose, organosulfate, fumed silica, magnesium stearate and polyethylene oxide.

In yet another embodiment, provided herein is a pharmaceutical composition comprising Compound A and one or more pharmaceutically acceptable excipients or carriers, each independently selected from pregelatinized starch, microcrystalline cellolose, sodium lauryl sulfate, silicon dioxide, magnesium stearate and polyethylene oxide.

In yet another embodiment, provided herein is a pharmaceutical composition comprising Compound A and one or more pharmaceutically acceptable excipients or carriers, each independently selected from pregelatinized starch, AVICEL® PH 101, sodium lauryl sulfate, colloidal silicon dioxide, magnesium stearate vegetable source and polyethylene oxide.

In one embodiment, provided herein is a pharmaceutical composition comprising Compound A, a diluent(s)/binder(s), a surfactant(s), a glidant(s), a lubricant(s) and a polymer(s).

In one embodiment, provided herein is a pharmaceutical composition comprising Compound A, starch and magnesium stearate.

In one embodiment, provided herein is a pharmaceutical composition comprising Compound A, starch, cellulose and magnesium stearate.

In another embodiment, provided herein is a pharmaceutical composition comprising Compound A, pregelatinized starch, microcrystalline cellulose, organosulfate, fumed silica and magnesium stearate.

In another embodiment, provided herein a pharmaceutical composition comprising Compound A, pregelatinized starch, microcrystalline cellulose, organosulfate, colloidal silicon dioxide, magnesium stearate and polyethylene oxide.

In still another embodiment, provided herein a pharmaceutical composition comprising Compound A, pregelatinized starch, AVICEL PH 102®, sodium lauryl sulfate, colloidal silicon dioxide, magnesium stearate and polyethylene oxide.

In one embodiment, provided herein is a pharmaceutical composition comprising about 10-30% by weight of Compound A, about 40-60% by weight of diluent(s)/binder(s), about 1-5% by weight of surfactant(s), about 1-5% by weight of glidant(s), about 0.1-2% by weight of lubricant(s) and about 20-50% by weight of polymer(s).

In one embodiment, provided herein is a pharmaceutical composition about 10-30% by weight of Compound A, about 10-30% by weight of starch, about 20-50% by weight of cellulose, about 0-10% by weight of organosulfate, about 1-5% by weight of fumed silica, about 0.1-2% by weight of maganesium stearate and about 10-50% by weight of polyethylene oxide.

In one embodiment, provided herein is a pharmaceutical composition comprising about 15% by weight of Compound A, about 49.5% by weight of diluent(s)/binder(s), about 3% by weight of surfactant(s), about 2% by weight of glidant(s), about 0.5% by weight of lubricant(s) and about 30% by weight of polymer(s).

In one embodiment, provided herein is a pharmaceutical composition comprising about 10-30% by weight of Compound A, about 10-30% by weight of starch, about 20-50% by weight of cellulose, about 1-5% by weight of organosulfate, about 1-5% by weight of fumed silica, about 0.1-2% by weight of maganesium stearate and about 20-50% by weight of polyethylene oxide.

In one embodiment, provided herein is a pharmaceutical composition comprising about 15% by weight of Compound A, about 20% by weight of starch, about 30% by weight of cellulose, about 3% by weight of organosulfate, about 2% by weight of fumed silica, about 1% by weight of magnesium stearate and about 30% by weight of polyethylene oxide.

In one embodiment, provided herein is a pharmaceutical composition comprising about 15% by weight of Compound A, about 20% by weight of starch, about 29.5% by weight of cellulose, about 3% by weight of organosulfate, about 2% by weight of fumed silica, about 0.5% by weight of magnesium stearate and about 30% by weight of polyethylene oxide.

In one embodiment, provided herein is a pharmaceutical composition comprising about 10-30% by weight of Compound A, about 10-30% by weight of pregelatinized starch, about 20-50% by weight of microcrystalline cellulose, about 1-5% by weight of sodium lauryl sulfate, about 1-5% by weight of silicon oxide, about 0.1-2% by weight of magnesium stearate and about 20-50% by weight of polyethylene oxide.

In one embodiment, provided herein is a pharmaceutical composition comprising about 15% by weight of Compound A, about 20% by weight of pregelatinized starch, about 30% by weight of microcrystalline cellulose, about 3% by weight of sodium lauryl sulfate, about 2% by weight of silicon oxide, about 1% by weight of maganesium stearate and about 30% by weight of polyethylene oxide.

In one embodiment, provided herein is a pharmaceutical composition comprising about 15% by weight of Compound A, about 20% by weight of pregelatinized starch, about 29.5% by weight of microcrystalline cellulose, about 3% by weight of of sodium lauryl sulfate, about 2% by weight of silicon oxide, about 0.5% by weight of maganesium stearate and about 30% by weight of polyethylene oxide.

In one embodiment, provided herein is a pharmaceutical composition comprising about 10-30% by weight of Compound A, about 10-30% by weight of pregelatinized starch, about 20-50% by weight of AVICEL® PH 101 or AVICEL® PH 102, about 1-5% by weight of sodium lauryl sulfate, about 1-5% by weight of colloidal silicon dioxide, about 0.1-2% by weight of magnesium stearate vegetable source and about 20-50% by weight of polyethylene oxide.

In one embodiment, provided herein is a pharmaceutical composition comprising about 15% by weight of Compound A, about 20% by weight of pregelatinized starch, about 29.5% by weight of AVICEL® PH 101 or AVICEL® PH 102, about 3% by weight of sodium lauryl sulfate, about 2% by weight of colloidal silicon dioxide, about 0.5% by weight of magnesium stearate vegetable source and about 30% by weight of polyethylene oxide.

In one embodiment, provided herein is a pharmaceutical composition comprising about 50-150 mg Compound A, about 100-500 mg diluent(s)/binder(s), about 10-30 mg surfactant(s), about 5-30 mg glidant(s), about 1-10 mg lubricant(s) and about 100-300 mg polymer(s).

In one embodiment, provided herein is a pharmaceutical composition comprising about 75 mg Compound A, about 247.5 mg diluent(s)/binder(s), about 15 mg surfactant(s), about 10 mg glidant(s), about 2.5 mg lubricant(s) and about 150 mg polymer(s).

In one embodiment, provided herein is a pharmaceutical composition comprising about 50-150 mg Compound A, about 50-150 mg starch, about 100-300 mg cellulose, about 10-30 mg organosulfate, about 5-30 mg fumed silica, about 1-10 mg maganesium stearate and about 100-300 mg polyethylene oxide.

In one embodiment, provided herein is a pharmaceutical composition comprising about 75 mg Compound A, about 100 mg starch, about 147.5 mg cellulose, about 15 mg organosulfate, about 10 mg fumed silica, about 2.5 mg maganesium stearate and about 150 mg polyethylene oxide.

In one embodiment, provided herein is a pharmaceutical composition comprising about 50-150 mg Compound A, about 50-150 mg pregelatinized starch, about 100-300 mg microcrystalline cellulose, about 10-30 mg sodium lauryl sulfate, about 5-30 mg silicon oxide, about 1-10 mg maganesium stearate and about 100-300 mg polyethylene oxide.

In one embodiment, provided herein is a pharmaceutical composition comprising about 75 mg Compound A, about 100 mg pregelatinized starch, about 147.5 mg microcrystalline cellulose, about 15 mg of sodium lauryl sulfate, about 10 mg silicon oxide, about 2.5 mg maganesium stearate and about 150 mg polyethylene oxide.

In one embodiment, provided herein is a pharmaceutical composition comprising about 50-150 mg Compound A, about 50-150 mg pregelatinized starch, about 100-300 mg AVICEL® PH 101 or AVICEL® PH 102, about 10-30 mg sodium lauryl sulfate, about 5-30 mg colloidal silicon dioxide, about 1-10 mg magnesium stearate vegetable source and about 100-300 mg polyethylene oxide.

In one embodiment, provided herein is a pharmaceutical composition comprising about 75 mg Compound A, about 100 mg pregelatinized starch, about 147.5 mg AVICEL® PH 101 or AVICEL® PH 102, about 15 mg of sodium lauryl sulfate, about 10 mg colloidal silicon dioxide, about 2.5 mg magnesium stearate vegetable source and about 150 mg polyethylene oxide.

Formulation J

In one embodiment, provided herein is a pharmaceutical composition comprising Formulations A and D.

In one embodiment, provided herein is a pharmaceutical composition comprising about 5-50% by weight of Formulation A, and about 50-95% by weight of Formulation D.

In one embodiment, provided herein is a pharmaceutical composition comprising about 35% by weight of Formulation A, and about 65% by weight of Formulation D.

In certain embodiments, provided herein are pharmaceutical compositions weighing about 200-1000 mg. In one embodiment, the pharmaceutical composition comprises about 50-300 mg Formulation A, and about 200-500 mg Formulation D.

In certain embodiments, provided herein are pharmaceutical compositions weighing about 445.2 mg. In one embodiment, the pharmaceutical composition comprises about 156 mg Formulation A and about 289.2 mg Formulation D.

In certain embodiments, provided herein are pharmaceutical compositions comprising about 5-50% by weight of a first component dosage form and about 50-95% by weight of a second component dosage form, wherein the first component dosage form comprises about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 15-45% by weight of a first component dosage form and about 55-85% by weight of a second component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation J is a multiparticulate formulation comprising discrete units (e.g., multiparticulates, minitabs or minitablets) of Formulations A and D.

Formulation K

In one embodiment, provided herein is a pharmaceutical composition comprising Formulations A and D.

In one embodiment, provided herein is a pharmaceutical composition comprising about 5-50% by weight of Formulation A, and about 50-95% by weight of Formulation D.

In one embodiment, provided herein is a pharmaceutical composition comprising about 38% by weight of Formulation A, and about 62% by weight of Formulation D.

In certain embodiments, provided herein are pharmaceutical compositions weighing about 200-1000 mg. In one embodiment, the pharmaceutical composition comprises about 50-300 mg Formulation A, and about 200-500 mg Formulation D.

In certain embodiments, provided herein are pharmaceutical compositions weighing about 406 mg. In one embodiment, the pharmaceutical composition comprises about 156 mg Formulation A and about 250 mg Formulation D.

In certain embodiments, provided herein are pharmaceutical compositions comprising about 5-50% by weight of a first component dosage form and about 50-95% by weight of a second component dosage form, wherein the first component dosage form comprises about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 20-50% by weight of a first component dosage form and about 50-80% by weight of a second component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation K is a multiparticulate formulation comprising discrete units (e.g., multiparticulates, minitabs or minitablets) of Formulations A and D.

Formulation L

In one embodiment, provided herein is a pharmaceutical composition comprising Formulation D.

In one embodiment, provided herein is a pharmaceutical composition comprising about 80-100% by weight of Formulation D.

In one embodiment, provided herein is a pharmaceutical composition comprising about 100% by weight of Formulation D.

In certain embodiments, provided herein are pharmaceutical compositions comprising dosage forms of Formulation D. In certain embodiments, provided herein are pharmaceutical compositions weighing about 200-800 mg. In certain embodiments, provided herein are pharmaceutical compositions comprising about 200-800 mg Formulation D.

In certain embodiments, provided herein are pharmaceutical compositions weighing about 400 mg. In certain embodiments, provided herein are pharmaceutical compositions comprising about 400 mg Formulation D.

In certain embodiments, provided herein are pharmaceutical compositions comprising about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 80-100% by weight of a component dosage form, wherein the component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation L is a multiparticulate formulation comprising discrete units (e.g., multiparticulates, minitabs or minitablets) of Formulation D.

Formulation M

In one embodiment, provided herein is a pharmaceutical composition comprising Formulations A and D.

In one embodiment, provided herein is a pharmaceutical composition comprising about 30-70% by weight of Formulation A, and about 30-70% by weight of Formulation D.

In one embodiment, provided herein is a pharmaceutical composition comprising about 47% by weight of Formulation A, and about 53% by weight of Formulation D.

In certain embodiments, provided herein are pharmaceutical compositions weighing about 200-1000 mg. In one embodiment, the pharmaceutical composition comprises about 50-300 mg Formulation A, and about 50-300 mg Formulation D.

In certain embodiments, provided herein are pharmaceutical compositions weighing about 439.4 mg. In one embodiment, the pharmaceutical composition comprises about 208 mg Formulation A and about 231.4 mg Formulation D.

In certain embodiments, provided herein are pharmaceutical compositions comprising about 30-70% by weight of a first component dosage form and about 30-70% by weight of a second component dosage form, wherein the first component dosage form comprises about 10-30% by weight of Compound A, about 40-50% by weight of lactose, about 20-30% by weight of cellulose, about 1-5% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 1-5% by weight of organosulfate, about 0.5-5% by weight of fumed silica, about 0.1-2% by weight of magnesium stearate, about 10-50% by weight of polyethylene oxide, about 1-10% by weight of ethylcellulose, about 1-10% by weight of Opadry as pore former and about 1-10% by weight of Opadry as coat.

In certain embodiments, provided herein are pharmaceutical compositions comprising about 40-60% by weight of a first component dosage form and about 40-60% by weight of a second component dosage form, wherein the first component dosage form comprises about 10-30% by weight of Compound A, about 40-50% by weight of lactose, about 20-30% by weight of cellulose, about 0-10% by weight of organosulfate, about 1-5% by weight of carboxymethyl cellulose, about 1-5% by weight of fumed silica, about 0.1-2% by weight of magnesium stearate and about 1-5% by weight of Opadry; and wherein the second component dosage form comprises about 5-30% by weight of Compound A, about 5-50% by weight of starch, about 5-40% by weight of cellulose, about 0-10% by weight of organosulfate, about 0.5-5% by weight of fumed silica, about 0.1-2% by weight of magnesium stearate, about 10-75% by weight of polyethylene oxide, about 1-20% by weight of ethylcellulose, about 0-20% by weight of Opadry as pore former and about 1-10% by weight of Opadry as coat.

In certain embodiments, the pharmaceutical compositions are capsule dosage forms.

In one embodiment, provided herein is a capsule dosage form suitable for administration in a size 4 or larger capsule.

In one embodiment, Formulation M is a multiparticulate formulation comprising discrete units (e.g., multiparticulates, minitabs or minitablets) of Formulations A and D.

6.2 Second Active Agents

In certain embodiments, provided herein are pharmaceutical compositions and dosage forms of Compound A, which may further comprise one or more secondary active ingredients. Certain combinations may work synergistically in the treatment of particular types diseases or disorders, and conditions and symptoms associated with such diseases or disorders. In certain embodiments, Compound A can also work to alleviate adverse effects associated with certain second active agents, and vice versa.

Specific second active compounds that can be contained in the formulations and dosage forms provided herein vary depending on the specific indication to be treated, prevented or managed.

For instance, for the treatment, prevention or management of cancer, second active agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa 2a; interferon alfa 2b; interferon alfa n1; interferon alfa n3; interferon beta I a; interferon gamma I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti cancer drugs include, but are not limited to: 20 epi 1,25 dihydroxyvitamin D3; 5 ethynyluracil; abiraterone; aclarubicin; acylfulvene; adecypenol; adozelesin; aldesleukin; ALL TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL 2; capecitabine; carboxamide amino triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubicin; ipomeanol, 4; iroplact; irsogladine; isobengazole; isohomohalicondrin B; itasetron; jasplakinolide; kahalalide F; lamellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anticancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum triamine complex; porfimer sodium; porfiromycin; prednisone; propyl bis acridone; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Additional embodiments of the second active compounds include, but not limited to: adalimumab, alefacept, azathioprine, certolizumab pegol, corticosteroids, cyclosporin, cyclosporine, diclofenac, efalizumab, etanercept, etodolac, golimumab, ibuprofen, indomethacin, infliximab, leflunomide, methotrexate, naproxen, nonsteroidal anti-inflammatory drugs, Opioid analgesics, phenylbutazone, retinoids, sulfasalazine, taclonex scalp, the biologics etanercept, tocilizumab, and ustekinumab.

Examples of such additional therapeutic agents include, but are not limited to: antihistamines including, but not limited to, ethanolamines, ethylenediamines, piperazines, and phenothiazines; antinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steriods including, but not limited to, cortical steroids, adrenocortical steroids, anti-inflammatory drugs, antihistamines and decongestants.

6.3 Process for Making Dosage Forms

Dosage forms provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of methylcellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet or capsule. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

In certain embodiments, provided herein are methods for preparing a composition provided herein, comprising: (i) weighing out the desired amount of Compound A and the desired amount of excipients; (ii) mixing or blending Compound A and the excipients; (iii) passing the mixture of Compound A and excipients through a screen; (iv) mixing or blending Compound A and the excipients after passage through the screen; (v) weighing out the desired amount of lubricating agents; (vi) passing the lubricating agents through a screen; (vii) mixing or blending Compound A the excipients and the lubricating agents; (viii) compressing the mixture of Compound A, the excipients and the lubricating agents; and (ix) coating the compressed mixture of Compound A, the excipients and the lubricating agents with a coating agent. In one embodiment, the excipient is lactose monohydrate. In another embodiment, the excipient is croscarmellose sodium. In yet another embodiment, the excipient is microcrystalline cellulose. In one embodiment, the screen is 18 mesh screen. In another embodiment, the screen is 1000 μm screen. In one embodiment, the screen is 30 mesh screen. In another embodiment, the screen is 600 μm screen. In one embodiment, the lubricating agent is stearic acid. In another embodiment, the lubricating agent is magnesium stearate. In one embodiment, the coating agent is Opadry clear. In another embodiment, the coating agent is Opadry pink. In another embodiment, the coating agent is Opadry yellow. In another embodiment, the coating agent is Opadry beige. In one embodiment, the mixture of Compound A, the excipients and the lubricating agents is compressed into a tablet form.

In certain embodiments, provided herein are methods for preparing a composition provided herein, comprising: (i) weighing out the desired amount of Compound A and the desired amount of excipients (such as lactose monohydrate, croscarmellose sodium and microcrystalline cellulose); (ii) passing the excipients through a screen (such as an 18 mesh or 1000 μm screen); (iii) mixing or blending Compound A and the excipients; (iv) passing the mixture of Compound A and excipients through a screen; (v) mixing or blending Compound A and the excipients; (vi) weighing out the desired amount of lubricating agents; (vii) passing the lubricating agents through a screen; (viii) mixing or blending Compound A, the excipients and the lubricating agents; (ix) compressing the mixture of Compound A, the excipients and the lubricating agents; and (x) coating the compressed mixture of Compound A, the excipients and the lubricating agents with a coating agent. In one embodiment, the screen is 18 mesh screen. In another embodiment, the screen is 1000 μm screen. In one embodiment, the screen is 30 mesh screen. In another embodiment, the screen is 600 μm screen. In one embodiment, the mixing or blending speed is 26 revolutions per minute. In one embodiment, the mixing or blending process lasts for 20 minutes. In one embodiment, the mixture of Compound A, the excipients and the lubricating agents is compressed into a tablet form. In one embodiment, the coating agent is Opadry clear. In another embodiment, the coating agent is Opadry pink. In another embodiment, the coating agent is Opadry yellow. In another embodiment, the coating agent is Opadry beige.

6.3.1 Screening

In one embodiment, the process for making the pharmaceutical compositions include the screening of the active ingredient and the excipient(s). In one embodiment, the active ingredient is passed through a screen having openings of about 200 microns to about 750 microns. In another embodiment, the active ingredient is passed through a screen with openings of about 200 microns to about 400 microns. In one embodiment, the active ingredient is passed through a screen having openings of about 300 to about 400 microns. Depending on the excipient(s) used, the screen openings vary. For example, disintegrants and binders are passed through openings of about 430 microns to about 750 microns, from about 600 microns to about 720 microns, or about 710 microns. Lubricants are typically passed through smaller openings, e.g., about 150 microns to about 250 microns screen. In one embodiment, the lubricant is passed through a screen opening of about 210 microns.

6.3.2 Pre-Blending

After the ingredients are screened, the excipient and active ingredient are mixed in a diffusion mixer. In one embodiment, the mixing time is from about 1 minute to about 50 minutes, from about 5 minutes to about 45 minutes, from about 10 minutes to about 40 minutes, or from about 10 minutes to about 25 minutes. In another embodiment, the mixing time is about 15 minutes.

When more than one excipients are used, the excipients may be admixed in a tumble blender for about 1 minute to about 20 minutes, or for about 5 minutes to about 10 minutes, prior to mixing with the active ingredient.

6.3.3 Roller Compaction

In one embodiment, the pre-blend may optionally be passed through a roller compactor with a hammer mill attached at the discharge of the compactor.

6.3.4 Final Blend

When a lubricant, e.g., magnesium stearate, vegetable source, is used, the lubricant is mixed with the pre-blend at the end of the process to complete the pharmaceutical composition. This additional mixing is from about 1 minute to about 10 minutes, or from about 3 minutes to about 5 minutes.

6.3.5 Encapsulation

The formulation mixture is then encapsulated into the desired size capsule shell using, for example, a capsule filling machine or a rotary tablet press.

6.4 Kits

Provided herein are kits which, when used by the medical practitioner, can simplify the administration of appropriate amounts of active ingredients to a patient.

In one embodiment, a kit comprises a unit dosage form of a compound provided herein, or a pharmaceutically acceptable solid form or prodrug thereof, and a unit dosage form of a second active ingredient. Examples of second active ingredients include, but are not limited to, those listed herein.

In other embodiments, a kit can further comprise devices that are used to administer the active ingredient(s). Examples of such devices include, but are not limited to, syringes, drip bags, patches, and inhalers.

In other embodiments, a kit can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6.5 Dissolution Profile

In certain embodiments, tablets or capsules comprising Compound A provided herein have a dissolution profile wherein about 100% of Compound A is released in about 1 hour, about 2 hours, about 3 hours, about 4 hours, about 5 hours, about 6 hours, about 7 hours, about 8 hours, about 9 hours, about 10 hours, about 11 hours, or about 12 hours in water, diluted HCl aqueous solution or other aqueous buffer solutions of about pH 1 to about pH 10 (e.g., about pH 3), with or without surfactant, with a paddle speed of 50 rpm or 75 rpm, or with a basket speed of 100 rpm or 150 rpm.

In certain embodiments, tablets or capsules comprising Compound A provided herein have a dissolution profile wherein about 50% of Compound A is released in about 2-4 hours in an aqueous solution of about pH 4.5 with a basket speed of 150 rpm.

In certain embodiments, tablets or capsules comprising Compound A provided herein have a dissolution profile wherein about 50% of Compound A is released in about 1-3 hours in an aqueous solution of about pH 4.5 with a basket speed of 150 rpm.

In certain embodiments, tablets or capsules comprising Compound A provided herein have a dissolution profile wherein about 50% of Compound A is released in about 1-2 hours in an aqueous solution of about pH 4.5 with a basket speed of 150 rpm.

In certain embodiments, tablets or capsules comprising Compound A provided herein have a dissolution profile wherein about 50% of Compound A is released in about 1-3 hours in an aqueous solution of about pH 4.5 with a basket speed of 150 rpm.

In certain embodiments, tablets or capsules comprising Compound A provided herein have a dissolution profile wherein about 50% of Compound A is released in about 5-7 hours in an aqueous solution of about pH 4.5 with a paddle speed of 75 rpm.

6.6 Methods of Treatment, Prevention, and Management

Provided herein are methods of treating, preventing, and/or managing certain diseases or disorders comprising administration of an effective amount of a composition or dosage form provided herein to a patient having said disease of disorder.

Examples of diseases or disorders that the compositions and dosage forms provided herein are useful for treating, preventing or managing include, but are not limited to: heart disease, such as congestive heart failure, cardiomyopathy, pulmonary edema, endotoxin mediated septic shock, acute viral myocarditis, cardiac allograft rejection, and myocardial infarction; solid tumors, including but not limited to, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma; and blood-born tumors including but not limited to, acute lymphoblastic leukemia "ALL", acute lymphoblastic B cell leukemia, acute lymphoblastic T cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, multiple myeloma and acute and chronic leukemias, for example, lymphoblastic, myelogenous, lymphocytic, and myelocytic leukemias.

Specific methods provided herein further comprise the administration of an additional therapeutic agent (i.e., a therapeutic agent other than apremilast). Examples of additional therapeutic agents include, but are not limited to, those listed herein.

Further provided herein are methods of treating or preventing diseases or disorders ameliorated by the inhibition of PDE4 in a patient which comprise administering to a patient in need of such treatment or prevention a therapeutically effective amount of stereomerically pure apremilast, or a pharmaceutically acceptable prodrug, metabolite, polymorph, salt, solvate, hydrate, or clathrate thereof. Disorders ameliorated by the inhibition of PDE4 include, but are not limited to, asthma, inflammation, chronic or acute obstructive pulmonary disease, chronic or acute pulmonary inflammatory disease, inflammatory bowel disease, Crohn's Disease, ankylosing spondylitis, Behcet's Disease, colitis, ulcerative colitis and arthritis (including psoriatic arthritis) or inflammation due to reperfusion. In a preferred embodiment, the disease or disorder to be treated or prevented is chronic obstructive pulmonary disease.

Specific methods provided herein can comprise the administration of an additional therapeutic agent such as, but not limited to, anti-inflammatory drugs, antihistamines and decongestants. Examples of such additional therapeutic agents include, but are not limited to: antihistamines including, but not limited to, ethanolamines, ethylenediamines, piperazines, and phenothiazines; antinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steriods including, but not limited to, cortical steroids and adrenocortical steroids.

Specific methods provided herein can avoid or reduce drug-drug interactions and other adverse effects associated with agents used in the treatment of such disorders, including racemic substituted phenylethylsulfones. Without being limited by any theory, stereomerically pure apremilast may further provide an overall improved therapeutic effectiveness, or therapeutic index, over racemic 2-[1-(3-ethoxy-4-methoxyphenyl)-2-methylsulfonylethyl]-4-acetylaminoisoindoline-1,3-dione. For example, a smaller amount of the drug may in some circumstances be administered to attain the same level of effectiveness.

In certain embodiments, the active compound (i.e., apremilast) may be used in the treatment or prevention of a wide range of diseases and conditions. The magnitude of a prophylactic or therapeutic dose of a particular active ingredient in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1000 mg per day, given as a single once-a-day dose preferably as divided doses throughout a day. More specifically, the daily dose is administered twice daily in equally divided doses. Specifically, a daily dose range should be from about 5 mg to about 500 mg per day, more specifically, between about 10 mg and about 200 mg per day. Specifically, the daily dose may be administered in 5 mg, 10 mg, 15 mg, 20 mg, 25 mg, 50 mg, 75 mg, 100 mg, 125 mg, 150 mg, 175 mg, and 200 mg dosage forms. In managing the patient, the therapy should be initiated at a lower dose, perhaps about 1 mg to about 25 mg, and increased if necessary up to about 200 mg to about 1000 mg per day as either a single dose or divided doses, depending on the patient's global response. Alternatively, the daily dose is from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

7. EXAMPLES

Embodiments provided herein may be more fully understood by reference to the following examples. These examples are meant to be illustrative of pharmaceutical compositions and dosage forms provided herein, but are not in any way limiting.

7.1 Example 1

Table 1 provides a dosage formulation for a 1.5 mg strength apremilast single unit dose immediate release (IR) minitablet that was prepared (Formulation A).

TABLE 1

Composition of IR Minitablets (Formulation A)

| Component | Function | mg/tablet |
|---|---|---|
| Apremilast | Active ingredient | 1.500 |
| Lactose monohydrate | Diluent | 3.388 |
| Microcrystalline cellulose | Diluent | 1.952 |
| Sodium lauryl sulfate | Surfactant | 0.226 |
| Croscarmellose sodium | Disintegrant | 0.226 |
| Colloidal silicon dioxide | Glidant | 0.152 |

TABLE 1-continued

Composition of IR Minitablets (Formulation A)

| Component | Function | mg/tablet |
|---|---|---|
| Magnesium stearate, Vegetable source | Lubricant | 0.056 |
| Total uncoated minitablet weight | | 7.500 |
| Opadry clear Water purified* | Coat | 0.300 |
| Total | | 7.800 |

*Removed during processing

7.2 Example 2

Table 2 provides a dosage formulation for a 1.5 mg strength apremilast single unit dose modified released (MR) minitablet coated with poly(methacrylic acid, ethyl acrylate, 1:1) that was prepared (Formulation B).

TABLE 2

Composition of MR Minitablets Coated with Poly(methacrylic acid, ethyl acrylate, 1:1) (Formulation B)

| Component | Function | mg/tablet |
|---|---|---|
| Apremilast | Active ingredient | 1.500 |
| Lactose monohydrate | Diluent | 3.388 |
| Microcrystalline cellulose | Diluent | 1.952 |
| Sodium lauryl sulfate | Surfactant | 0.226 |
| Croscarmellose sodium | Disintegrant | 0.226 |
| Colloidal silicon dioxide | Glidant | 0.152 |
| Magnesium stearate, Vegetable source | Lubricant | 0.056 |
| Total uncoated minitablet weight | | 7.500 |
| Opadry clear Water purified* | Coat | 0.300 |
| Total seal coated minitablet weight | | 7.800 |
| Poly(methacrylic acid, ethyl acrylate) white Triethyl citrate Water purified* | Polymer/ Modified release coat Plasticizer | 2.836 0.284 |
| Total poly(methacrylic acid, ethyl acrylate) coated minitab | | 10.920 |
| Opadry clear Water purified* | Coat | 0.328 |
| Total | | 11.248 |

*Removed during processing

7.3 Example 3

Table 3 provides a dosage formulation for a 1.5 mg strength apremilast single unit dose modified released (MR) minitablet coated with poly(methyl acrylate, methyl methacrylate, methacrylic acid, 7:3:1) that was prepared (Formulation C).

TABLE 3

Composition of MR Minitablets Coated with Poly(methyl acrylate, methyl methacrylate, methacrylic acid, 7:3:1) (Formulation C)

| Component | Function | mg/tablet |
|---|---|---|
| Apremilast | Active ingredient | 1.500 |
| Lactose monohydrate | Diluent | 3.388 |
| Microcrystalline cellulose | Diluent | 1.952 |
| Sodium lauryl sulfate | Surfactant | 0.226 |
| Croscarmellose sodium | Disintegrant | 0.226 |
| Colloidal silicon dioxide | Glidant | 0.152 |
| Magnesium stearate, Vegetable source | Lubricant | 0.056 |
| Total uncoated minitablet weight | | 7.500 |
| Opadry clear Water purified* | Coat | 0.300 |
| Total seal coated minitablet weight | | 7.800 |
| Poly(methyl acrylate, methyl methacrylate, methacrylic acid) | Polymer/ Modified release coat | 0.421 |
| Triethyl citrate Water purified* | Plasticizer | 0.047 |
| Total | | 8.268 |

*Removed during processing

7.4 Example 4

Table 4 provides a dosage formulation for a 1.5 mg strength apremilast single unit dose modified released (MR) matrix minitablet coated with ethylcellulose that was prepared (Formulation D).

TABLE 4

Composition of MR Matrix Minitablets Coated with Ethylcellulose (Formulation D)

| Component | Function | mg/tablet |
|---|---|---|
| Apremilast | Active ingredient | 1.500 |
| Microcrystalline cellulose | Diluent | 2.218 |
| Polyethylene oxide | Polymer/ Modified release component | 2.256 |
| Pregelatinized starch | Diluent | 1.128 |
| Sodium lauryl sulfate | Surfactant | 0.226 |
| Colloidal silicon dioxide | Glidant | 0.150 |
| Magnesium stearate, Vegetable source | Lubricant | 0.038 |
| Total uncoated minitablet weight | | 7.516 |
| Opadry clear Water purified* | Coat | 0.301 |
| Total seal coated minitablet weight | | 7.817 |
| Ethylcellulose clear | Polymer/ Modified release coat | 0.564 |

TABLE 4-continued

Composition of MR Matrix Minitablets Coated with Ethylcellulose (Formulation D)

| Component | Function | mg/tablet |
|---|---|---|
| Opadry clear | Pore former | 0.062 |
| Water purified* | | |
| Total ethylcellulose coated minitab | | 8.443 |
| Opadry clear | Coat | 0.253 |
| Water purified* | | |
| Total | | 8.696 |

*Removed during processing

7.5 Example 5

Table 5 provides a dosage formulation for a 75 mg strength apremilast single dose MR unit in a size #0 capsule that was prepared (Formulation E).

TABLE 5

Composition of Apremilast (or Compound A) 75 mg MR Capsules (Formulation E)

| Minitablet population | E |
|---|---|
| IR Minitablet (A) | 0 mg |
| MR Minitablet coated with Poly(methacrylic acid, ethyl acrylate, 1:1) (B) | 0 mg |
| MR Minitablet coated with Poly(methyl acrylate, methyl methacrylate, methacrylic acid, 7:3:1) (C) | 0 mg |
| MR Matrix Minitablets Coated with Ethylcellulose (D) | 434 mg |
| Size 0 White Gelatin Capsule | 1 unit |

Figure 4:
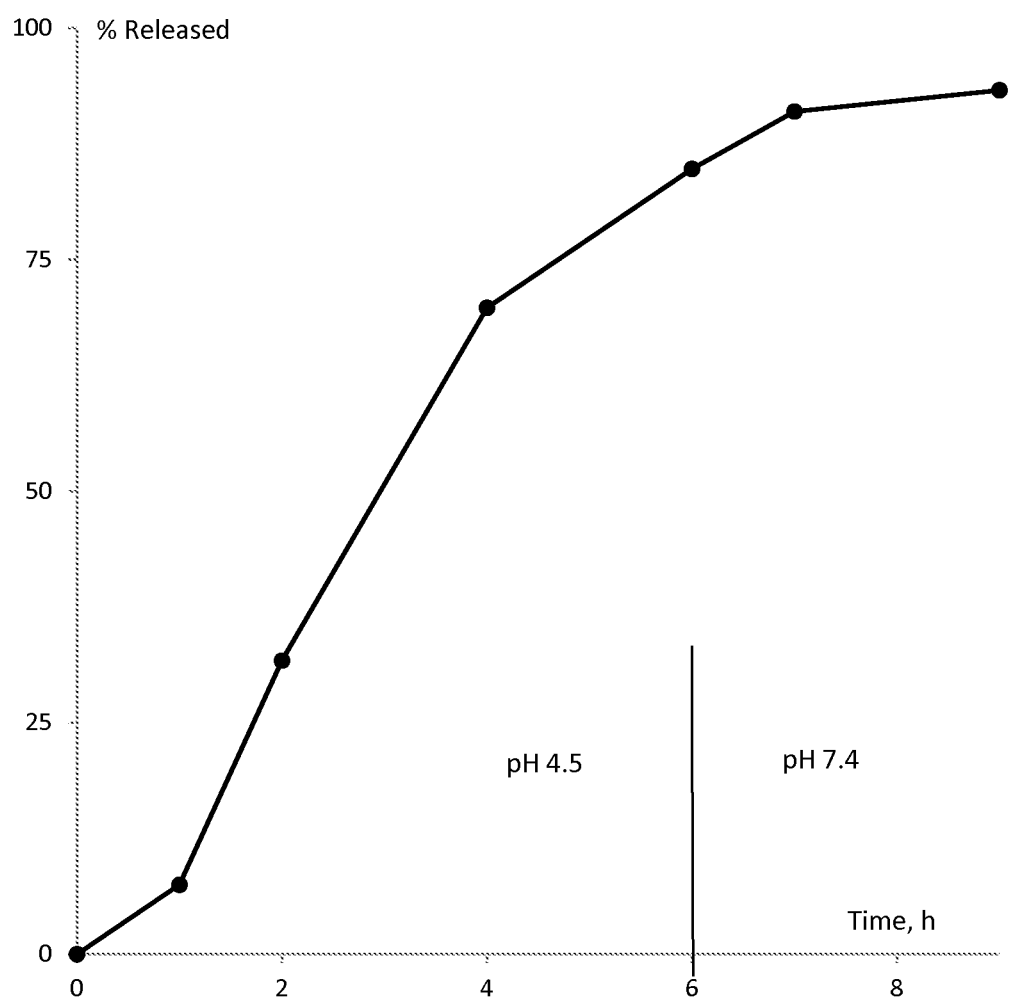
FIG. 4: Dissolution profile for Formulation E.

Dissolution profile is provided in FIG. 4. The dissolution profile of Formulation E is measured in an aqueous solution with 0.5% wt sodium lauryl sulfate with a basket speed of 150 rpm. The pH of the aqueous solution is 4.5 for 6 hours after the measurement starts, and then adjusted to 7.4.

7.6 Example 6

Table 6 provides a dosage formulation for a 75 mg strength apremilast single dose MR unit in a size #0 capsule that was prepared (Formulation F).

TABLE 6

Composition of Apremilast (or Compound A) 75 mg MR Capsules (Formulation F)

| Minitablet population | F |
|---|---|
| IR Minitablet (A) | 78 mg |
| MR Minitablet coated with Poly(methacrylic acid, ethyl acrylate, 1:1) (B) | 0 mg |
| MR Minitablet coated with Poly(methyl acrylate, methyl methacrylate, methacrylic acid, 7:3:1) (C) | 0 mg |
| MR Matrix Minitablets Coated with Ethylcellulose (D) | 347 mg |
| Size 0 White Gelatin Capsule | 1 unit |

Figure 5:
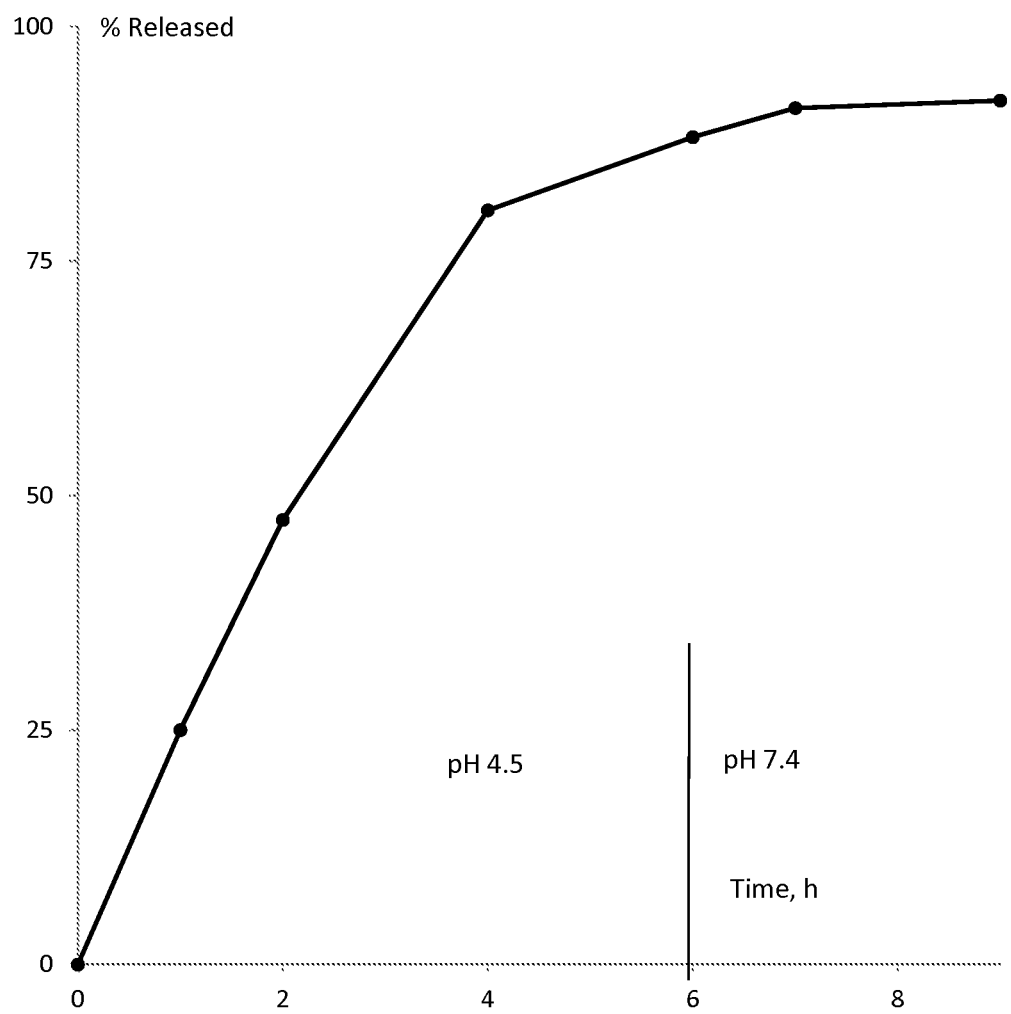
FIG. 5: Dissolution profile for Formulation F.

Dissolution profile is provided in FIG. 5. The dissolution profile of Formulation F is measured in an aqueous solution with 0.5% wt sodium lauryl sulfate with a basket speed of 150 rpm. The pH of the aqueous solution is 4.5 for 6 hours after the measurement starts, and then adjusted to 7.4.

7.7 Example 7

Table 7 provides a dosage formulation for a 75 mg strength apremilast single dose MR unit in a size #0 capsule that was prepared (Formulation G).

TABLE 7

Composition of Apremilast (or Compound A) 75 mg MR Capsules (Formulation G)

| Minitablet population | G |
|---|---|
| IR Minitablet (A) | 146 mg |
| MR Minitablet coated with Poly(methacrylic acid, ethyl acrylate, 1:1) (B) | 90 mg |
| MR Minitablet coated with Poly(methyl acrylate, methyl methacrylate, methacrylic acid, 7:3:1) (C) | 193 mg |
| MR Matrix Minitablets Coated with Ethylcellulose (D) | 0 mg |
| Size 0 White Gelatin Capsule | 1 unit |

Dissolution profile is provided in FIG. 6. The dissolution profile of Formulation G is measured in an aqueous solution with 0.5% wt sodium lauryl sulfate with a basket speed of 150 rpm. The pH of the aqueous solution is 4.5 for 2 hours after the measurement starts, and then adjusted to 7.4. The dissolution profile of Formulation G indicates a pH dependent release process.

7.8 Example 8

Table 8 provides a dosage formulation for a 75 mg strength apremilast single dose MR unit in a size #0 capsule that was prepared (Formulation H).

TABLE 8

Composition of Apremilast (or Compound A) 75 mg MR Capsules (Formulation H)

| Minitablet population | H |
|---|---|
| IR Minitablet (A) | 104 mg |
| MR Minitablet coated with Poly(methacrylic acid, ethyl acrylate, 1:1) (B) | 0 mg |
| MR Minitablet coated with Poly(methyl acrylate, methyl methacrylate, methacrylic acid, 7:3:1) (C) | 55 mg |
| MR Matrix Minitablets Coated with Ethylcellulose (D) | 260 mg |
| Size 0 White Gelatin Capsule | 1 unit |

Dissolution profile is provided in FIG. 7. The dissolution profile of Formulation H is measured in an aqueous solution with 0.5% wt sodium lauryl sulfate with a basket speed of 150 rpm. The pH of the aqueous solution is 4.5 for 6 hours after the measurement starts, and then adjusted to 7.4. The dissolution profile of Formulation H indicates a pH dependent release process.

7.9 Example 9

Table 9 provides a dosage formulation for a 75 mg strength apremilast single unit dose modified release (MR) tablet that was prepared (Formulation I).

TABLE 9

Composition of 75 mg Apremilast MR Tablets (Formulation I)

| Component | Function | Quality Standard | mg/ tablet | Batch Formula |
|---|---|---|---|---|
| Apremilast | Active ingredient | In-house | 75.0 | 450.0 |
| Microcrystalline cellulose | Diluent | NF | 147.5 | 885.0 |
| Pregelatinized starch | Diluent | NF | 100.0 | 600.0 |
| Polyethylene oxide | Polymer/ Modified release component | NF | 150.0 | 900.0 |
| Sodium lauryl sulfate | Surfactant | NF | 15.0 | 90.0 |
| Colloidal silicon dioxide | Glidant | NF | 10.0 | 60.0 |
| Magnesium stearate, Vegetable source | Lubricant | NF | 2.5 | 15.0 |
| Total | | | 500.0 | 3000.0 |

Figure 8:
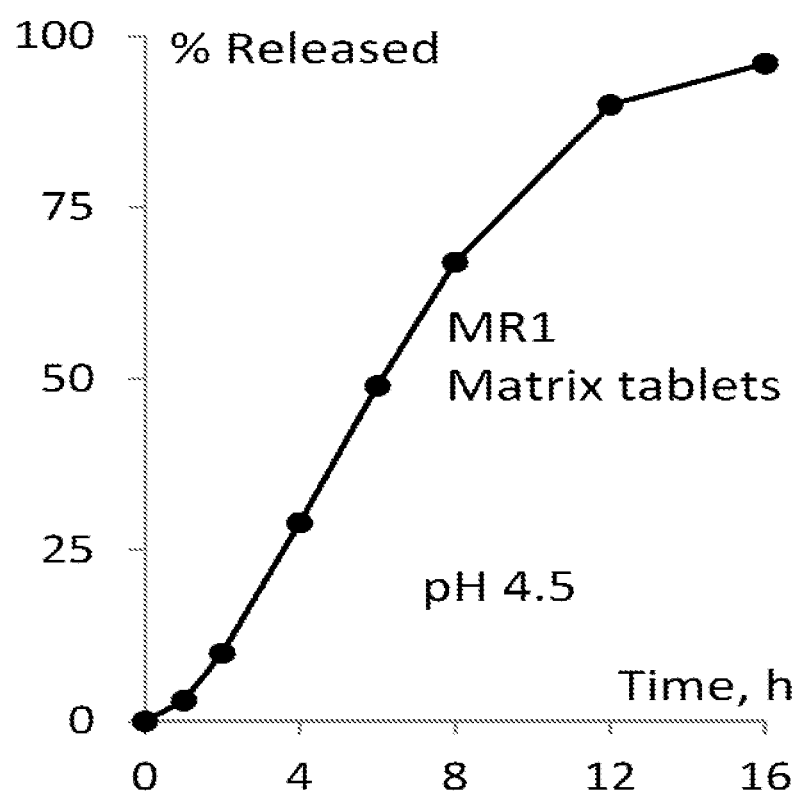
FIG. 8: Dissolution profile for Formulation I.

Dissolution profile is provided in FIG. 8. The dissolution profile of Formulation I is measured in an aqueous solution with 0.3% wt sodium lauryl sulfate with a paddle speed of 75 rpm. The pH of the aqueous solution is 4.5.

7.10 Example 10

Table 10 provides dosage formulations for single dose MR units in a size #0 capsule with 80 mg strength apremilast (Formulations J, K, L, M).

TABLE 10

Composition of Apremilast (or Compound A) MR Capsules (Formulations J, K, L, M)

| Minitablet population | J | K | L | M |
|---|---|---|---|---|
| IR Minitablet (A) | 156 mg | 156 mg | 0 mg | 208 mg |
| MR Matrix Minitablets with or without ethylcellulose coate (D) | 289.2 mg | 250 mg | 400 mg | 231.4 mg |
| Size 0 White Gelatin Capsule | 1 unit | 1 unit | 1 unit | 1 unit |
| Apremilast strength | 80 mg | 80 mg | 80 mg | 80 mg |

7.11 Example 11

As described in FIG. 1, a manufacturing process for the 75 mg apremilast modified release (MR) tablet comprises steps of: (1) loading microcrystalline cellulose, apremilast drug substance, polyethylene oxide, pregelatinized starch, sodium lauryl sulfate and silicon dioxide in a blender and blending; (2) screening the blend from step 1, loading the screened blend in the blender and blending; (3) screening magnesium stearate, loading the screened magnesium stearate and the blend in the blender from step 2 and blending; and (4) compressing the blend from step 3 to tablets.

7.12 Example 12

Figure 2:
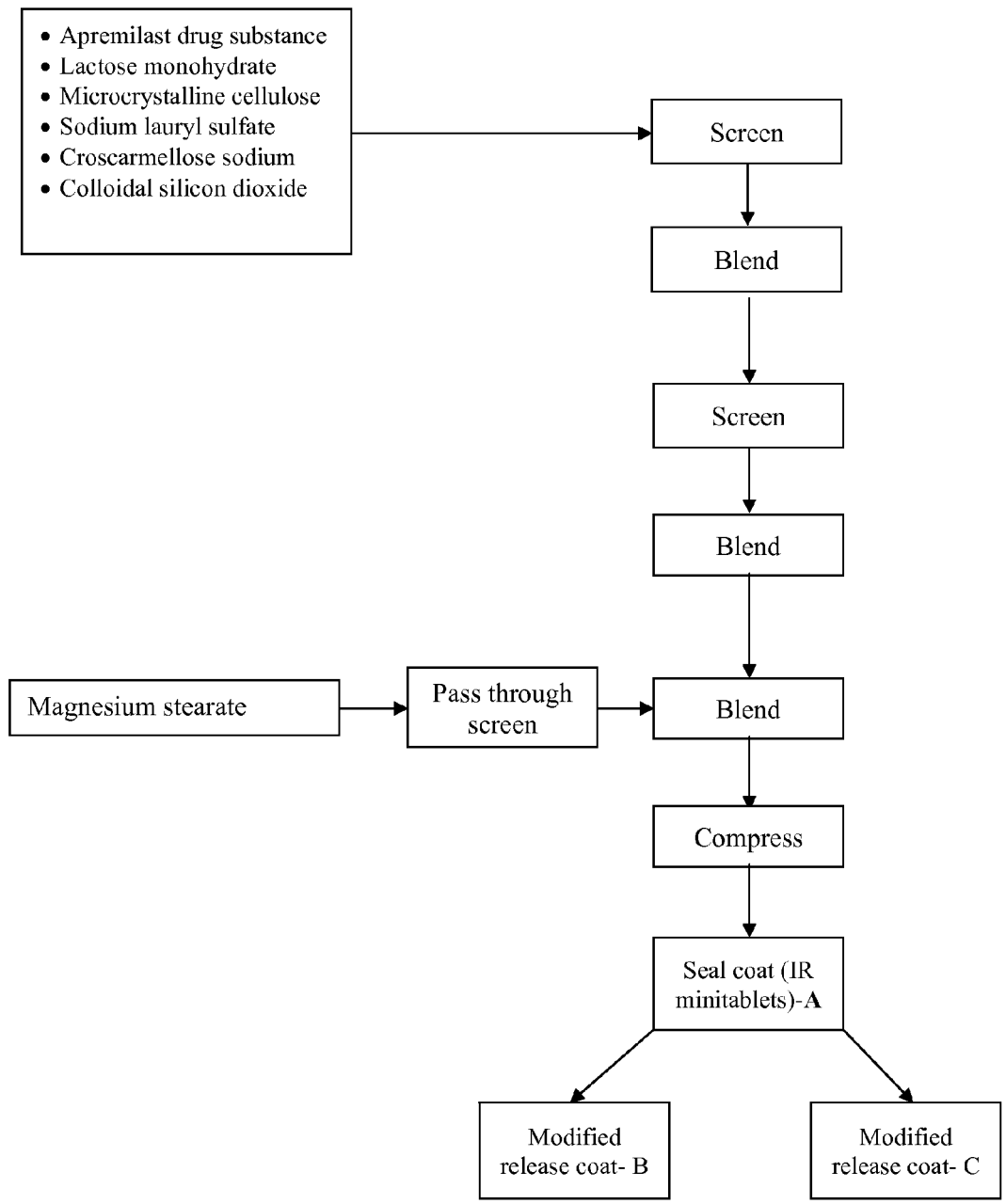
FIG. 2: Process flow diagram for the manufacture of apremilast immediate release (IR) minitablets coated with modified release coat.

As described in FIG. 2, a manufacturing process for apremilast immediate release (IR) minitablets coated with modified release coat comprises steps of: (1) screening apremilast drug substance, lactose monohydrate, microcrystalline cellulose, sodium lauryl sulfate, croscarmellose sodium, and colloidal silicon dioxide, loading the screened mixture in a blender and blending; (2) screening the blend from step 1, loading the screened mixture in the blender and blending; (3) screening magnesium stearate, loading the screened magnesium stearate and the blender from step 2 in the blender and blending; (4) compressing the blender from step 3 to minitablets; (5) seal coating the minitablets from step 4 with Opadry; and (6) coating the seal coated minitablets from step 5 with poly(methacrylic acid, ethyl acrylate) and/or poly(methyl acrylate, methyl methacrylate, methacrylic acid).

7.13 Example 13

Figure 3:
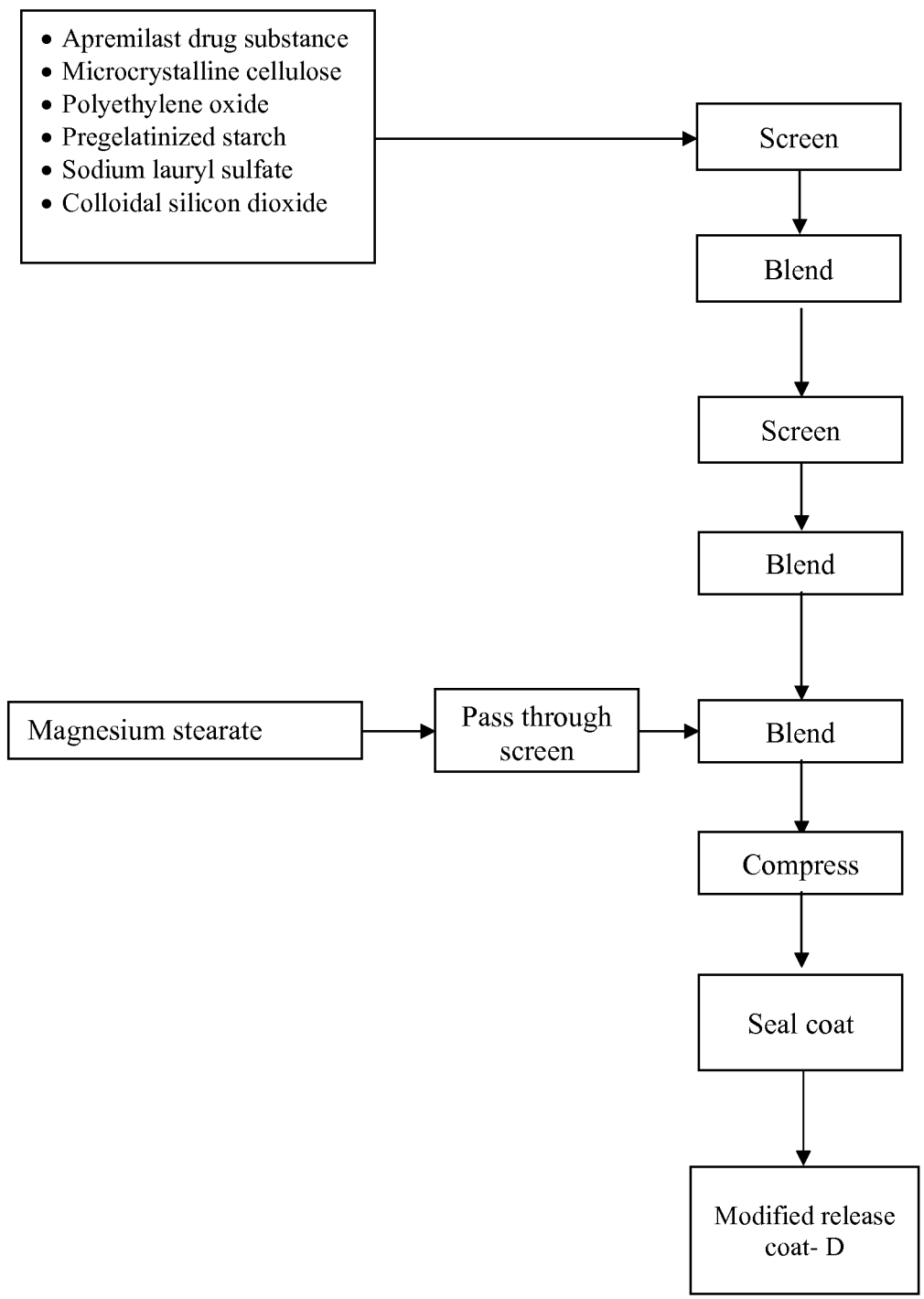
FIG. 3: Process flow diagram for the manufacture of apremilast matrix minitablets coated with modified release coat.

As described in FIG. 3, a manufacturing process for apremilast modified released (MR) matrix minitablets coated with modified release coat comprises steps of: (1) screening apremilast drug substance, microcrystalline cellulose, polyethylene oxide, pregelatinized starch, sodium lauryl sulfate, and colloidal silicon dioxide, loading the screened mixture in a blender and blending; (2) screening the blend from step 1, loading the screened blend in a blender and blending; (3) screening magnesium stearate, load the screened magnesium stearate and the blender from step 2 and blending; (4) compressing the blend from step 3 to minitablets; (5) seal coating the minitablets from step 4 with Opadry; and (6) coating the coated minitablets from step 5 with ethylcellulose.

7.14 Example 14

A manufacturing process for a apremilast MR formulation for administration in a capsule comprises: 1) mixing different amount of minitablets provided herein; and (2) encapsulating the mixture from step 1 into a size 1 or larger capsule.

While examples of certain particular embodiments are provided herein, it will be apparent to those skilled in the art that various changes and modifications may be made. Such modifications are also intended to fall within the scope of the appended claims.

What is claimed is:

1. An immediate-release oral dosage form comprising about 10-30% by weight of apremilast, about 40-50% by weight of lactose, about 20-30% by weight of cellulose, about 1-5% by weight of carboxymethyl cellulose, about 1-5% by weight of fumed silica and about 0.1-2% by weight of magnesium stearate and about 1-5% by weight of a coat, wherein about 100% of said apremilast is released in about 1 hour in an aqueous buffer solution of about pH 3 with a paddle speed of 75 rpm.

2. The oral dosage form of claim 1 comprising about 19% by weight of apremilast, about 43% by weight of lactose monohydrate, about 25% by weight of microcrystalline cellulose, about 3% by weight of sodium lauryl sulfate, about 3% by weight of croscarmellose sodium, about 2% by weight of colloidal silicon dioxide and about 1% by weight of magnesium stearate and about 4% by weight of a coat.

3. The oral dosage form of claim 1, further comprising about 0-10% by weight of sodium lauryl sulfate.

* * * * *